US012180266B2

(12) United States Patent
Cooper et al.

(10) Patent No.: US 12,180,266 B2
(45) Date of Patent: *Dec. 31, 2024

(54) MODIFIED HAEMOGLOBIN PROTEINS

(71) Applicant: University of Essex Enterprises Limited, Colchester (GB)

(72) Inventors: Chris E. Cooper, Colchester (GB); Brandon Reeder, Colchester (GB); Gary Silkstone, Colchester (GB)

(73) Assignee: University of Essex Enterprises Limited, Colchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/493,654

(22) PCT Filed: Mar. 13, 2018

(86) PCT No.: PCT/GB2018/050626
§ 371 (c)(1),
(2) Date: Sep. 12, 2019

(87) PCT Pub. No.: WO2018/167469
PCT Pub. Date: Sep. 20, 2018

(65) Prior Publication Data
US 2020/0131247 A1  Apr. 30, 2020

(30) Foreign Application Priority Data
Mar. 13, 2017 (GB) .................... 1704006

(51) Int. Cl.
*C07K 14/805* (2006.01)
*A61P 9/10* (2006.01)
*A61K 38/00* (2006.01)

(52) U.S. Cl.
CPC .............. *C07K 14/805* (2013.01); *A61P 9/10* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 6,812,207 B1 | 11/2004 | Olson et al. | |
| 6,967,020 B2 | 11/2005 | Tsuchida et al. | |
| 8,609,814 B2* | 12/2013 | Cooper | A61P 7/00 530/385 |
| 11,529,421 B2 | 12/2022 | Cooper et al. | |
| 2006/0088583 A1 | 4/2006 | Takeoka et al. | |
| 2010/0105606 A1 | 4/2010 | Winslow et al. | |
| 2010/0137189 A1* | 6/2010 | Cooper | A61K 47/62 514/13.4 |

FOREIGN PATENT DOCUMENTS

| | | |
|---|---|---|
| EP | 0561245 A1 | 9/1993 |
| WO | WO-9202239 A1 | 2/1992 |
| WO | WO-0198356 A1 | 12/2001 |
| WO | WO-2009004309 A1 | 1/2009 |
| WO | WO-2012006101 A2 | 1/2012 |
| WO | WO-2018167469 A1 | 9/2018 |

OTHER PUBLICATIONS

Panchenko et al. ('Prediction of functional sites by analysis of sequence and structure conservation' Protein Science v13 2004 pp. 884-892) (Year: 2004).*
Uniprot entry for P28781 (retrieved from https://www.uniprot.org/uniprot/P28781 on Mar. 8, 2022; data entered Dec. 1, 1992, 6 pages) (Year: 1992).*
HBG1 sequence (retrieved from https://www.ncbi.nlm.nih.gov/protein/AKI70719.1#comment_AKI70719.1 on Sep. 22, 2022, database entry 2015, 2 pages) (Year: 2015).*
"International Application PCT/GB2018/050626, International Search and Written Opinion mailed Jun. 8, 2018", (Jun. 8, 2018), 26 pgs.
"United Kingdom Application GB1704006.4, Search Report dated Jan. 8, 2018", (Jan. 8, 2018), 6 pgs.
Alayash, Abdu I., et al., "Reactions of Sperm Whale Myoglobin with Hydrogen Peroxide: Effects of Distal Pocket Mutations on the Formation and Stability of the Ferryl Intermediate", The Journal of Biological Chemistry, vol. 274, No. 4, Issue of Jan. 22, pp. 2029-2037, 1999, (Jan. 22, 1999), 2029-2037.
Battistuzzi, Gianantonio, et al., "Redox reactivity of the heme Fe3+/Fe2+ couple in native myoglobins and mutants with peroxidaselike activity", JBIC Journal of Biological Inorganic Chemistry, vol. 12, No. 7 [abstract only], (Jun. 19, 2007), 951-958.
Bisse, Emmanuel, et al., "Characterization of a New Electrophoretically Silent Hemoglobin Variant", The Journal of Biological Chemistry, vol. 275, No. 28, Issue of Jul. 14, pp. 21380-21384, 2000, (Apr. 18, 2000), 21380-21384.
Carver, Theodore, et al., "A Novel Site-directed Mutant of Myoglobin with an Unusually High O2 Affinity and Low Autooxidation Rate", The Journal of Biological Chemistry, vol. 267, No. 20, Issue of Jul. 15, pp. 14443-14450, 1992, (Jul. 15, 1992), 14443-14450.
Griffon, Nathalie, et al., "Tetramer-dimer equilibrium of oxyhemoglobin mutants determined from auto-oxidation rates", Protein Science, Wiley, US, vol. 7, No. 3, (Mar. 1, 1998), 673-680.
Jensen, Michael, et al., "Hemoglobin Syracuse (alpha2beta2-143(H21)His leads to Pro), a new high-affinity variant detected by special electrophoretic methods: observations on the auto-oxidation of normal and variant hemoglobins", Journal of Clinical Investigation, vol. 55, No. 3, (Mar. 1, 1975), 469-477.

(Continued)

Primary Examiner — Ronald T Niebauer
(74) Attorney, Agent, or Firm — Schwegman Lundberg & Woessner, P.A.

(57) ABSTRACT

The present invention relates to modified proteins e.g. oxygen-carrying proteins, with improved or enhanced, in comparison to a reference protein, reduction of a metal ion associated with the modified protein. The present invention also relates to methods of using such modified proteins and compositions comprising such proteins e.g. in therapy.

8 Claims, 14 Drawing Sheets

Specification includes a Sequence Listing.

(56) References Cited

OTHER PUBLICATIONS

Jeong, S. T., et al., "Recombinant hemoglobin(alpha 29leucine --> phenylalanine, alpha 96valine --> tryptophan, beta 108asparagine --> lysine) exhibits low oxygen affinity and high cooperativity combined with resistance to autoxidation", Biochemistry, vol. 38, No. 40, 13433-13442 [abstract only], (Oct. 5, 1999), 13433-13442.

Kiger, Laurent, et al., "Trematode Hemoglobins Show Exceptionally High Oxygen Affinity", Biophysical Journal, vol. 75, No. 2, Aug. 1998, 990-998, (Aug. 1, 1998), 990-998.

Reeder, Brandon J., et al., "Tyrosine Residues as Redox Cofactors in Human Hemoglobin: Implications for Engineering NonToxic Blood Substitutes", Journal of Biological Chemistry, vol. 283, No. 45, (Nov. 7, 2008), 30780-30787.

Saitou, Naruya, et al., "The Neighbor-Joining Method: A New Method for Reconstructing Phylogenetic Trees", Mo. Biol. Evol. 4(4):406-425 (1987), (1987), 406-425.

Shibata, Tomokazu, et al., "Relationship between Oxygen Affinity and Autoxidation of Myoglobin", Inorganic Chemistry, vol. 51, No. 21, (Oct. 12, 2012), 11955-11960.

Silkstone, Gary G.A., et al., "Engineering tyrosine electron transfer pathways decreases oxidative toxicity in hemoglobin: implications for blood substitute design", Biochemical Journal, vol. 473, No. 19, epub Jul. 2016, 3371-3383, (Jul. 28, 2016), 3371-3383.

Silkstone, R. S., "The betaLys66Tyr Variant of Human Hemoglobin as a Component of a Blood Substitute", In: Elwell C.E., Leung T.S., harrison D.K. (eds) Oxygen Transport to Tissue XXXVII, Advances in Experimental Medicine and Biology: Oxygen Transport to Tissue, vol. 876, Springer, New York, NY [abstract only], (2006), 455-460.

Thom, Christopher S., et al., "Hemoglobin Variants: Biochemical Properties and Clinical Correlates", Cold Spring Harb Perspect Med 2013;3:a011858, (Feb. 6, 2013), 22 pgs.

Wiltrout, M. E., et al., "A biophysical investigation of recombinant hemoglobins with aromatic B10 mutations in the distal heme pockets", Biochemistry, vol. 44, No. 19, May 2005, 7207-7217 [abstract only], (May 2005), 7207-7217.

"International Application PCT/GB2018/050626, International Preliminary Report on Patentability dated Sep. 17, 2019", 21 pgs.

Reeder, Brandon, et al., "Modulating Electron Transfer Pathways in Hemoglobin", Abstract 47, Metals, Metalloproteins and Redox Reactions, Free Radical Biology and Medicine, vol. 43 (Suppl. 1, No. 47), (2007), p. S27.

"European Application No. 18711670.2, Communication pursuant to Article 94(3) EPC dated Jun. 14, 2021", (Jun. 14, 2021), 24 pgs.

"Human hemoglobin subunit beta", Database UniProt [Online], XP055811973, retrieved from www.uniprot.org accession No. P68871; Database accession No. HBB_HUMAN, (Feb. 15, 2017), 44 pgs.

"The zebrafish reference genome sequence and its relationship to the human genome", Database UniProt [Online], XP055811938, retrieved from www.uniprot.org accession No. Q90486; Database accession No. HBB1_DANRE, (Feb. 15, 2017), 4 pgs.

\* cited by examiner

SEQ. ID. NO. 1: HUMAN HAEMOGLOBIN BETA CHAIN SUBUNIT
```
         10         20         30         40         50         60
VHLTPEEKSA VTALWGKVNV DEVGGEALGR LLVVYPWTQR FFESFGDLST PDAVMGNPKV
         70         80         90        100        110        120
KAHGKKVLGA FSDGLAHLDN LKGTFATLSE LHCDKLHVDP ENFRLLGNVL VCVLAHHFGK
        130        140
EFTPPVQAAY QKVVAGVANA LAHKYH
```

SEQ. ID. NO. 2: HUMAN HAEMOGLOBIN BETA CHAIN SUBUNIT
```
         10         20         30         40         50         60
VLSPADKTNV KAAWGKVGAH AGEYGAEALE RMFLSFPTTK TYFPHFDLSH GSAQVKGHGK
         70         80         90        100        110        120
KVADALTNAV AHVDDMPNAL SALSDLHAHK LRVDPVNFKL LSHCLLVTLA AHLPAEFTPA
        130        140
VHASLDKFLA SVSTVLTSKY R
```

SEQ. ID. NO. 3 HEMOGLOBIN GAMMAL
```
GHFTEEDKA TITSLWGKVN VEDAGGETLG RLLWYPWTQ RFFDSFGNLS
SASAIMGNPK VKAHGKKVLT SLGDAIKHLD DLKGTFAQLS ELHCDKLHVD
PENFKLLGNV LVTVLAIHFG KEFTPEVQAS WQKMVTAVAS ALSSRYH
```

SEQ. ID. NO. 4: HUMAN HAEMOGLOBIN GAMMA 2 (GAMMAG) CHAIN SUBUNIT
```
         10         20         30         40         50         60
GHFTEEDKAT ITSLWGKVNV EDAGGETLGR LLVVYPWTQR FFDSFGNLSS ASAIMGNPKV
         70         80         90        100        110        120
KAHGKKVLTS LGDAIKHLDD LKGTFAQLSE LHCDKLHVDP ENFKLLGNVL VIVLAIHFGK
        130        140
EFTPEVQASW QKMVTGVASA LSSRYH
```

SEQ. ID. NO. 5: HUMAN HAEMOGLOBIN BETA CHAIN SUBUNIT (V1M)
```
         10         20         30         40         50         60
MHLTPEEKSA VTALWGKVNV DEVGGEALGR LLVVYPWTQR FFESFGDLST PDAVMGNPKV
         70         80         90        100        110        120
KAHGKKVLGA FSDGLAHLDN LKGTFATLSE LHCDKLHVDP ENFRLLGNVL VCVLAHHFGK
        130        140
EFTPPVQAAY QKVVAGVANA LAHKYH
```

FIG. 8

SEQ. ID. NO. 6: HAEMOGLOBIN ALPHA CHAIN SUBUNIT (V1M)

```
          10         20         30         40         50         60
MLSPADKTNV KAAWGKVGAH AGEYGAEALE RMFLSFPTTK TYFPHFDLSH GSAQVKGHGK
          70         80         90        100        110        120
KVADALTNAV AHVDDMPNAL SALSDLHAHK LRVDPVNFKL LSHCLLVTLA AHLPAEFTPA
         130        140
VHASLDKFLA SVSTVLTSKY R
```

SEQ. ID. NO. 7 HEMOGLOBIN GAMMA1 G1M

MHFTEEDKAT ITSLWGKVNV EDAGGETLGR LLVVYPWTQR FFDSFGNLSS
ASAIMGNPKV KAHGKKVLTS LGDAIKHLDD LKGTFAQLSE LHCDKLHVDP
ENFKLLGNVL VTVLAIHFGK EFTPEVQASW QKMVTAVASA LSSRYH

SEQ. ID. NO. 8: HAEMOGLOBIN GAMMA 2 (GAMMAG) CHAIN SUBUNIT (G1M)

```
          10         20         30         40         50         60
MHFTEEDKAT ITSLWGKVNV EDAGGETLGR LLVVYPWTQR FFDSFGNLSS ASAIMGNPKV
          70         80         90        100        110        120
KAHGKKVLTS LGDAIKHLDD LKGTFAQLSE LHCDKLHVDP ENFKLLGNVL VTVLAIHFGK
         130        140
EFTPEVQASW QKMVTGVASA LSSRYH
```

SEQ. ID. NO. 9: MODIFIED HAEMOGLOBIN BETA CHAIN SUBUNIT (βT84Y)

```
          10         20         30         40         50         60
VHLTPEEKSA VTALWGKVNV DEVGGEALGR LLVVYPWTQR FFESFGDLST PDAVMGNPKV
          70         80         90        100        110        120
KAHGKKVLGA FSDGLAHLDN LKGYFATLSE LHCDKLHVDP ENFKLLGNVL VCVLAHHFGK
         130        140
EFTPPVQAAY QKVVAGVANA LAHKYH
```

SEQ. ID. NO. 10: MODIFIED HAEMOGLOBIN BETA CHAIN SUBUNIT (V1M: βT84Y)

```
          10         20         30         40         50         60
MHLTPEEKSA VTALWGKVNV DEVGGEALGR LLVVYPWTQR FFESFGDLST PDAVMGNPKV
          70         80         90        100        110        120
KAHGKKVLGA FSDGLAHLDN LKGYFATLSE LHCDKLHVDP ENFRLLGNVL VCVLAHHFGK
         130        140
EFTPPVQAAY QKVVAGVANA LAHKYH
```

FIG. 9

SEQ. ID. NO. 12: HAEMOGLOBIN ALPHA CHAIN SUBUNIT (αL91Y)
```
         10         20         30         40         50         60
VLSPADKTNV KAAWGKVGAH AGEYGAEALE RMFLSFPTTK TYFPHFDLSH GSAQVKGHGK
         70         80         90        100        110        120
KVADALTNAV AHVDDMPNAL SALSDLHAHK YRVDPVNFKL LSHCLLVTLA AHLPAEFTPA
        130        140
VHASLDKFLA SVSTVLTSKY R
```

SEQ. ID. NO. 11: MODIFIED HAEMOGLOBIN ALPHA CHAIN SUBUNIT (V1M; αL91Y)
```
         10         20         30         40         50         60
MLSPADKTNV KAAWGKVGAH AGEYGAEALE RMFLSFPTTK TYFPHFDLSH GSAQVKGHGK
         70         80         90        100        110        120
KVADALTNAV AHVDDMPNAL SALSDLHAHK YRVDPVNFKL LSHCLLVTLA AHLPAEFTPA
        130        140
VHASLDKFLA SVSTVLTSKY R
```

SEQ. ID. NO. 13: MODIFIED HAEMOGLOBIN GAMMA 2 (GAMMAG) CHAIN SUBUNIT (G1M; γ2L96Y)
```
         10         20         30         40         50         60
MHFTEEDKAT ITSLWGKVNV EDAGGETLGR LLVVYPWTQR FFDSFGNLSS ASAIMGNPKV
         70         80         90        100        110        120
KAHGKKVLTS LGDAIKHLDD LKGTFAQLSE LHCDKYHVDP ENFKLLGNVL VTVLAIHFGK
        130        140
EFTPEVQASW QKMVTGVASA LSSRYH
```

SEQ. ID. NO. 14: MODIFIED HAEMOGLOBIN ALPHA CHAIN SUBUNIT (V1M; αL29F)
```
         10         20         30         40         50         60
MLSPADKTNV KAAWGKVGAH AGEYGAEAFE RMFLSFPTTK TYFPHFDLSH GSAQVKGHGK
         70         80         90        100        110        120
KVADALTNAV AHVDDMPNAL SALSDLHAHK LRVDPVNFKL LSHCLLVTLA AHLPAEFTPA
        130        140
VHASLDKFLA SVSTVLTSKY R
```

SEQ. ID. NO. 15: MODIFIED HAEMOGLOBIN GAMMA 2 (GAMMAG) CHAIN SUBUNIT (G1M; γ2V67F)
```
         10         20         30         40         50         60
MHFTEEDKAT ITSLWGKVNV EDAGGETLGR LLVVYPWTQR FFDSFGNLSS ASAIMGNPKV
         70         80         90        100        110        120
KAHGKKFLTS LGDAIKHLDD LKGTFAQLSE LHCDKLHVDP ENFKLLGNVL VTVLAIHFGK
        130        140
EFTPEVQASW QKMVTGVASA LSSRYH
```

FIG. 10

SEQ. ID. NO. 16: MODIFIED HAEMOGLOBIN ALPHA CHAIN SUBUNIT (V1M; αL29F; αL91Y)

```
         10         20         30         40         50         60
MLSPADKTNV KAAWGKVGAH AGEYGAEAFE RMFLSFPTTK TYFPHFDLSH GSAQVKGHGK
         70         80         90        100        110        120
KVADALTNAV AHVDDMPNAL SALSDLHAHK YRVDPVNFKL LSHCLLVTLA AHLPAEFTPA
        130        140
VHASLDKFLA SVSTVLTSKY R
```

SEQ. ID. NO. 17: MODIFIED HAEMOGLOBIN GAMMA 2 (GAMMAG) CHAIN SUBUNIT (G1M; γ22V67F; γ2L96Y)

```
         10         20         30         40         50         60
MHFTEEDKAT ITSLWGKVNV EDAGGETLGR LLVVYPWTQR FFDSFGNLSS ASAIMGNPKV
         70         80         90        100        110        120
KAHGKKFLTS LGDAIKHLDD LKGTFAQLSE LHCDKYHVDP ENFKLLGNVL VTVLAIHFGK
        130        140
EFTPEVQASW QKMVTGVASA LSSRYH
```

SEQ. ID. NO. 18: HUMAN MYOGLOBIN

```
         10         20         30         40         50         60
GLSDGEWQLV LNVWGKVEAD IPGHGQEVLI RLFKGHPETL EKFDKFKHLK SEDEMKASED
         70         80         90        100        110        120
LKKHGATVLT ALGGILKKKG HHEAEIKPLA QSHATKHKIP VKYLEFISEC IIQVLQSKHP
        130        140        150
GDFGADAQGA MNKALELFRK DMASNYKELG FQG
```

FIG. 11

MODIFIED HAEMOGLOBIN PROTEINS

PRIORITY CLAIM TO RELATED APPLICATIONS

This application is a U.S. national stage filing under 35 U.S.C. § 371 from International Application No. PCT/GB2018/050626, filed on 13 Mar. 2018, and published as WO2018/167469 on 20 Sep. 2018, which claims the benefit under 35 U.S.C. 119 to United Kingdom Application No. GB 1704006.4, filed on 13 Mar. 2017, the benefit of priority of each of which is claimed herein, and which applications and publication are hereby incorporated herein by reference in their entirety.

FIELD OF THE INVENTION

Certain aspects of the present invention relate to modified proteins e.g. oxygen-carrying proteins, with improved or enhanced, in comparison to a reference protein, reduction of a metal ion associated with the modified protein. Also included herein are methods of using such modified proteins and compositions comprising such proteins e.g. in therapy.

BACKGROUND TO THE INVENTION

In cases where major blood loss occurs or blood flow is reduced, such as in cases of where blood flow is reduced due to blood loss due to trauma, disease or ischemia, tissue damage and organ dysfunction can occur due to oxygen deprivation of the cells and tissue leading to hypoxia, anoxia and in some cases cell death.

The use of blood transfusions (red blood cell transfusion) can help transport oxygenated blood through the major blood vessels but not always to smaller capillaries and the microvasculature meaning that these may remain collapsed and in an ischemic condition even after treatment with expanders, drugs or by a blood transfusion.

There also exist a number of issues with red blood cell transfusions. In some cases, blood for use in a red blood cell transfusion may not be readily available such as on the battlefield, in pre-hospital emergency treatment and during major civil crises involving mass casualties. The shelf-life of donated blood and its stringent handling needs also mean that suitable donated blood may not be readily available for transfusion. Issues also arise where patients have rare blood types that are not easily matched or may not accept blood transfusions for religious or personal reasons.

One solution to these problems is the use of a blood substitute. A blood substitute is an oxygen carrying solution that can help to maintain the oncotic pressure needed to maintain blood volume and transport oxygen to cells and tissue around the body therefore helping prevent oxygen deprivation (hypoxia) and ischemia.

Blood substitutes can act as an oxygenation bridge till red blood cell transfusion or in some cases used instead of red blood cell transfusion. It is also possible to use the oxygen carrying constituent of a blood substitute as an oxygen therapeutic. An oxygen therapeutic can be used to help improve the oxygen carrying ability of a patient's blood as well as improving the oxygen carrying capabilities of blood used for transfusions when administered in addition to red blood cells. Oxygen therapeutics as part of a blood substitute or as part of other fluids can be used in a number of methods wherein oxygen may be required such as in the storage of organs as well as in the treatment of carbon monoxide poisoning and in cell culture methods as well.

There are currently two main types of oxygen carrying therapeutics undergoing studies, fluorocarbon emulsions and haemoglobin based oxygen carriers (HBOCs).

Adult haemoglobin in its native environment of a red blood cell is a tetrameric protein composed of two alpha and two beta globin chain subunits, each subunit carrying a haem molecule. One alpha-like globin chain and one beta-like globin chain combine to form a stable dimer. The two dimers are then aligned in an anti-parallel fashion to form a tetramer. The binding between dimers in the tetramer is not as strong as monomers binding to form dimers. Therefore tetramers have a tendency to dissociate back to dimers. At high globin concentrations the tetramer form is the most common but when diluted dimers are the most predominant form.

A disadvantage associated with the use of native haemoglobin as an oxygen therapeutic is that the tetrameric form readily dissociates into the dimeric form which is rapidly cleared by the kidneys causing damage to the kidneys and renal system.

In order to address this disadvantage, a number of haemoglobin variants which prevent dissociation of the tetramer and that are more stable have been designed. Another approach has been to modify the protein by the addition of polymers to improve stability.

Another disadvantage of HBOCs has been spontaneous oxidation of the haem iron atom under physiological conditions. The haem iron atom is converted from the active oxygen carrying ferrous ($Fe^{2+}$) oxy-haem form to the non-functional (non-oxygen carrying) ferric ($Fe^{3+}$) met-haem form. This oxidation can also produce a superoxide ion ($O_2^-$) which subsequently dismutates rapidly to $H_2O_2$. The $H_2O_2$ if not degraded by catalases can react with the $Fe^{3+}$ ion to produce a highly reactive and cytotoxic ferryl ($Fe^{4+}$) haem form and protein based free radicals. This oxidative cascade can be damaging as $H_2O_2$ is a powerful oxidant known to produce cellular damage and the ferryl haem and protein based free radicals can initiate oxidation of lipids, nucleic acids and amino acids within the cell. The free radicals produced can also lead to damage to the protein and the haem group, which can cause the release of one or more haem groups which can have a number of adverse effects on cells such as causing inflammation.

It has been previously shown that it is possible to increase reduction of the ferryl haem form to the non-functional ferric met-haem form by the introduction of redox-active amino acid residues at specific locations into the protein therefore reducing toxicity of HBOCs. The mutations are believed to introduce an electron transport pathway not previously present in certain haemoglobin chain subunits or certain other haemoglobin like proteins. It was found though that these mutations did not lead to further reduction of the non-functional ferric met-haem form to the functional ferrous oxy-haem form. Therefore, these mutated HBOCs displayed lower toxicity but no improved oxygen carrying capability.

These disadvantages associated with prior HBOC oxygen therapeutics mean that there is a still a need for HBOCs with improved oxygen carrying capability as well as reduced toxicity.

It is an aim of certain embodiments of the present invention to at least partly mitigate the above-mentioned problems associated with the prior art.

It is an aim of certain embodiments of the present invention to provide a blood substitute which comprises a modified oxygen-carrying protein having enhanced reduction of a metal ion associated with the modified protein.

It is an aim of certain embodiments of the present invention to provide a blood substitute which comprises a modified oxygen-carrying protein having an enhanced rate at which an oxidised form of the modified oxygen-carrying protein is capable of re-oxygenation to an oxygen-binding form as compared to a reference protein.

It is an aim of certain embodiments of the present invention to provide an improved oxygen therapeutic.

It is an aim of certain embodiments of the present invention to provide an oxygen therapeutic with reduced cytotoxicity.

It is an aim of certain embodiments of the present invention to provide an oxygen therapeutic with increased oxygen carrying capability.

It is an aim of certain embodiments of the present invention to provide an oxygen therapeutic with reduced cytotoxicity and increased oxygen carrying capability.

SUMMARY OF THE INVENTION

In a first aspect of the present invention there is provided a modified oxygen-carrying protein comprising at least one modification, wherein said modification introduces or enhances reduction of at least one metallic ion and increases a rate at which an oxidised form of the modified oxygen-carrying protein is capable of re-oxygenation to an oxygen-binding form as compared to a reference protein.

In certain embodiments, the reference protein is a wild-type protein.

In certain embodiments, the at least one metallic ion is an iron ion. In certain embodiments, the at least one iron ion is a ferric ($Fe^{3+}$) ion. Thus, in certain embodiments, the modified protein exhibits an enhanced rate of reduction of a ferric ($Fe^{3+}$) ion to a ferrous ($Fe^{2+}$) ion.

In certain embodiments, the modified protein is a globin protein. In certain embodiments, the modified protein is a mammalian globin e.g. a human globin. In alternative embodiments, the modified protein is a non-human mammalian globin.

In certain embodiments, the modified protein is a haemoglobin. In certain embodiments, the modified protein is a mammalian haemoglobin e.g. a human haemoglobin. In certain embodiments, the modified protein is an adult haemoglobin. In certain embodiments, the modified protein is a foetal haemoglobin. In alternative embodiments, the modified protein is a non-human mammalian haemoglobin.

In certain embodiments, the modified protein is a haemoglobin chain subunit. In certain embodiments the modified protein is haemoglobin beta chain subunit. In certain embodiments, the modified protein is haemoglobin alpha chain subunit. In certain embodiments, the modified protein is haemoglobin gamma chain subunit. In certain embodiments, the modified protein is haemoglobin gamma 1 chain subunit. In certain embodiments, the modified protein is haemoglobin gamma 2 chain subunit. In certain embodiments, the reference protein is a human haemoglobin beta chain subunit with an amino acid sequence as set forth in SEQ ID NO: 1 or SEQ ID NO: 5. In certain embodiments, the reference protein is a human haemoglobin alpha chain subunit with an amino acid sequence as set forth in SEQ ID NO: 2 or SEQ ID NO: 6. In certain embodiments, the reference protein is a human haemoglobin gamma 1 chain subunit with an amino acid sequence as set forth in SEQ ID NO: 3 or SEQ ID NO: 7. In certain embodiments, the reference protein is a human haemoglobin gamma 2 chain subunit with an amino acid sequence as set forth in SEQ ID NO: 4 or SEQ ID NO: 8.

In certain embodiments, the at least one modification is an insertion of at least one redox-active amino acid residue and/or at least one substitution of an amino acid residue of the modified protein with at least one redox-active amino acid residue. In certain embodiments, the at least one redox-active amino acid is tyrosine. In certain embodiments, the at least one redox-active amino acid is histidine. In certain embodiments, the at least one redox-active amino acid is tryptophan. In certain embodiments, the at least one redox-active amino acid is phenylalanine.

In certain embodiments, the at least one modification is a plurality of modifications as described herein.

In certain embodiments, the modified protein further comprises at least one further modification. In certain embodiments, the at least one further modification is a plurality of further modifications.

In a second aspect of the present invention there is provided a composition comprising;
a modified oxygen-carrying protein comprising at least one modification, wherein said modification introduces or enhances reduction of at least one metallic ion and increases a rate at which an oxidised form of the modified oxygen-carrying protein is capable of re-oxygenation to an oxygen-binding form as compared to a reference protein; and
a pharmaceutically acceptable carrier or diluent.

In certain embodiments, the composition further comprises at least one reductant. In certain embodiments, the at least one reductant is ascorbate.

In certain embodiments, the composition comprises a modified protein as described herein and a pharmaceutically acceptable carrier or diluent.

In certain embodiments, the composition is a pharmaceutical composition. In certain embodiments, the composition is a blood substitute composition.

In a further aspect of the present invention, there is provided a method of treating and/or preventing ischemia and/or hypoxia comprising:
administering a pharmaceutically effective amount of a modified oxygen-carrying protein comprising at least one modification, wherein said modification introduces or enhances reduction of at least one metallic ion and increases a rate at which an oxidised form of the modified oxygen-carrying protein is capable of re-oxygenation to an oxygen-binding form as compared to a reference protein or a pharmaceutical composition comprising the modified protein.

In certain embodiments, the method comprises administering a pharmaceutically effective amount of a pharmaceutical composition as described herein.

In another aspect of the present invention there is provided a composition as described herein for use as a medicament.

In certain embodiments, the composition is for use in the treatment of ischemia. In certain embodiments, the composition is for use in the treatment of hypoxia. In certain embodiments, the composition is for use in the treatment of ischemia and/or hypoxia.

In a further aspect of the present invention there is provided a modified protein as described herein for use as a medicament.

In a further aspect of the present invention there is provided a modified protein as described herein for use as an oxygen therapeutic.

In a further aspect of the present invention there is provided a modified protein as described herein for use in the treatment of ischemia and/or hypoxia. In certain embodiments, the modified protein is for use in the treatment of ischemia. In certain embodiments, the modified protein is for use in the treatment of hypoxia.

Further details of certain embodiments are provided below.

BRIEF DESCRIPTION OF DRAWINGS

Certain embodiments of the present invention will now be described hereinafter, by way of example only, with reference to the accompanying drawings in which:

FIG. 8 illustrates the amino acid sequences of:
wild-type human haemoglobin beta chain subunit (SEQ ID NO: 1);
wild-type human haemoglobin alpha chain subunit (SEQ ID NO: 2);
wild-type human haemoglobin gamma 1 chain subunit (also known as gammaA) (SEQ ID NO: 3);
wild-type human haemoglobin gamma 2 chain subunit (also known as gammaG) (SEQ ID NO: 4); and
haemoglobin beta chain with the modification V1M (SEQ ID NO: 5);

FIG. 9 illustrates the amino acid sequences of:
haemoglobin alpha chain with the modification V1M (SEQ ID NO: 6);
haemoglobin gamma 1 chain subunit with the modification G1M (SEQ ID NO: 7);
haemoglobin gamma 2 chain subunit with the modification G1M (SEQ ID NO: 8);
haemoglobin beta chain subunit with the modification T84Y (SEQ ID NO: 9); and
haemoglobin beta chain subunit with modifications V1M and T84Y (SEQ ID NO:10);

FIG. 10 illustrates the amino acid sequences of:
haemoglobin alpha chain subunit with the modification V1M and L91Y (SEQ ID NO: 11);
haemoglobin alpha chain subunit with the modification L91Y (SEQ ID NO: 12);
haemoglobin gamma 2 chain subunit with modifications G1M and L96Y (SEQ ID NO: 13);
haemoglobin alpha chain subunit with the modifications V1M and L29F (SEQ ID NO: 14); and
haemoglobin gamma 2 chain subunit with the modifications G1M and V67F (SEQ ID NO: 15); and FIG. 11 illustrates the amino acid sequences of:
haemoglobin alpha chain subunit with the modifications V1M, L29F and L91Y (SEQ ID NO: 16);
haemoglobin gamma 2 chain subunit with the modifications G1M, V67F and L96Y (SEQ ID NO: 17); and
human myoglobin (SEQ ID NO: 18).

DETAILED DESCRIPTION OF THE CERTAIN EMBODIMENTS

Figure 1:
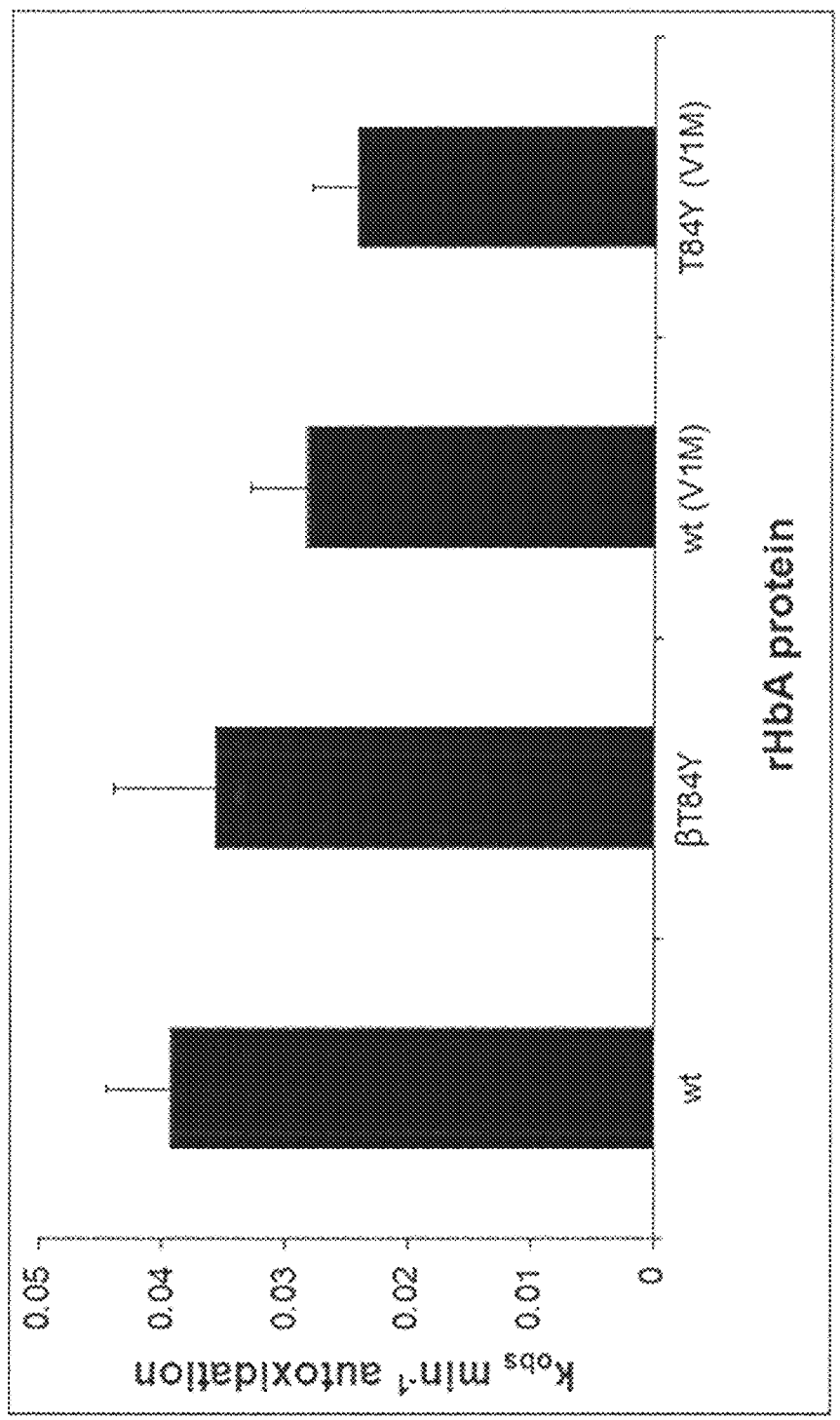
FIG. 1 illustrates the rate of autoxidation of 10 μM of recombinant adult haemoglobin (HbA) ferrous oxy-haemoglobin to ferric met-haemoglobin for various reference proteins (wild-type HbA (wt) and V1M modified wild-type HbA (wt V1M)), the βT84Y modified protein and βT84Y (V1M) modified protein in sodium phosphate buffer (20 mM, pH 7.2) at a temperature of 37° C. Each bar is an average of 6 repeat experiments. The standard deviations are shown by the error bars. Rate traces were fitted to single exponentials.

Further features of certain embodiments of the present invention are described below.

The practice of embodiments of the present invention will employ, unless otherwise indicated, conventional techniques of molecular biology, microbiology, recombinant DNA technology and immunology, which are within the skill of those working in the art.

Most general molecular biology, microbiology recombinant DNA technology and immunological techniques can be found in Sambrook et al, Molecular Cloning, A Laboratory Manual (2001) Cold Harbor-Laboratory Press, Cold Spring Harbor, N.Y. or Ausubel et al., Current protocols in molecular biology (1990) John Wiley and Sons, N.Y. Unless defined otherwise, all technical and scientific terms used herein have the same meaning as commonly understood by one of ordinary skill in the art to which this disclosure belongs. For example, the Concise Dictionary of Biomedicine and Molecular Biology, Juo, Pei-Show, $2^{nd}$ ed., 2002, CRC Press; The Dictionary of Cell and Molecular Biology, $3^{rd}$ ed., Academic Press; and the Oxford University Press, provide a person skilled in the art with a general dictionary of many of the terms used in this disclosure.

Units, prefixes and symbols are denoted in their Système International de Unitese (SI) accepted form. Numeric ranges are inclusive of the numbers defining the range. Unless otherwise indicated, amino acid sequences are written left to right in amino to carboxy orientation. All amino acid residues in proteins of embodiments of the invention are preferably of the L-configuration. However, D-configuration amino acids may also be present.

In a broad aspect, the present disclosure relates to modified oxygen-carrying proteins with an introduced or enhanced metallic ion reduction activity as compared to a reference protein and uses thereof.

As used herein the term "oxygen-carrying protein" refers to any polypeptide chain that in its native state is able, alone or in complex with other molecules and/or polypeptides, to bind to oxygen, transport oxygen and subsequently release oxygen bound to the protein, therefore is a polypeptide that releasably binds to oxygen. Oxygen-carrying proteins that may be modified as is disclosed herein may be recombinant proteins as well as any synthetically engineered proteins where the protein has been engineered so as to releasably bind oxygen. In some embodiments, the protein is an isolated, recombinant, substantially pure, or non-naturally occurring oxygen-carrying protein.

As used herein the terms "polypeptide" and "protein" are terms that are used interchangeably to refer to a polymer of amino acids, without regard to the length of the polymer. Typically, polypeptides and proteins have a polymer length that is greater than that of "peptides."

As used herein, the term "wild-type" refers to an amino acid sequence or nucleic acid sequence that is a native or naturally-occurring sequence. As used herein, the term "naturally-occurring" refers to anything (e.g., proteins, amino acids, or nucleic acid sequences) that are found in nature. Conversely, the term "non-naturally occurring" refers to anything that is not found in nature (e.g., recombinant nucleic acids and protein sequences produced in the laboratory or modifications of the wild-type sequence). In certain embodiments, the wild-type protein is a human haemoglobin beta chain subunit as set forth in SEQ ID NO: 1. In certain embodiments, the wild-type protein is a human haemoglobin alpha chain subunit as set forth in SEQ ID NO: 2. In certain embodiments, the wild-type protein is a human haemoglobin gamma 1 chain subunit (also known as gamma-A) as set forth in SEQ ID NO: 3. In certain embodiments, the wild-type protein is a human haemoglobin gamma 2 chain subunit (also known as gamma-G) as set forth in SEQ ID NO: 4.

As used herein, the terms "modified" and "modification" refer to substitution, addition or deletion of an amino acid residue or amino acid residues, and includes substitutions with or additions of any of the 20 amino acids commonly found in human proteins, as well as atypical or non-naturally occurring amino acids.

In certain embodiments of the present invention the modified protein may have an introduced or enhanced metallic ion reduction activity as compared to a "reference protein".

In certain embodiments, the modified protein may comprise an insertion of at least one redox-active amino acid residue and/or at least one substitution of an amino acid residue of the modified protein with at least one redox-active amino acid residue, wherein the insertion and/or substitution introduces or enhances reduction of at least one iron ion. Typically, the modified protein exhibits enhanced reduction of a ferric ($Fe^{3+}$) ion to a ferrous ($Fe^{2+}$) ion—as compared to a reference protein.

Figure 13:
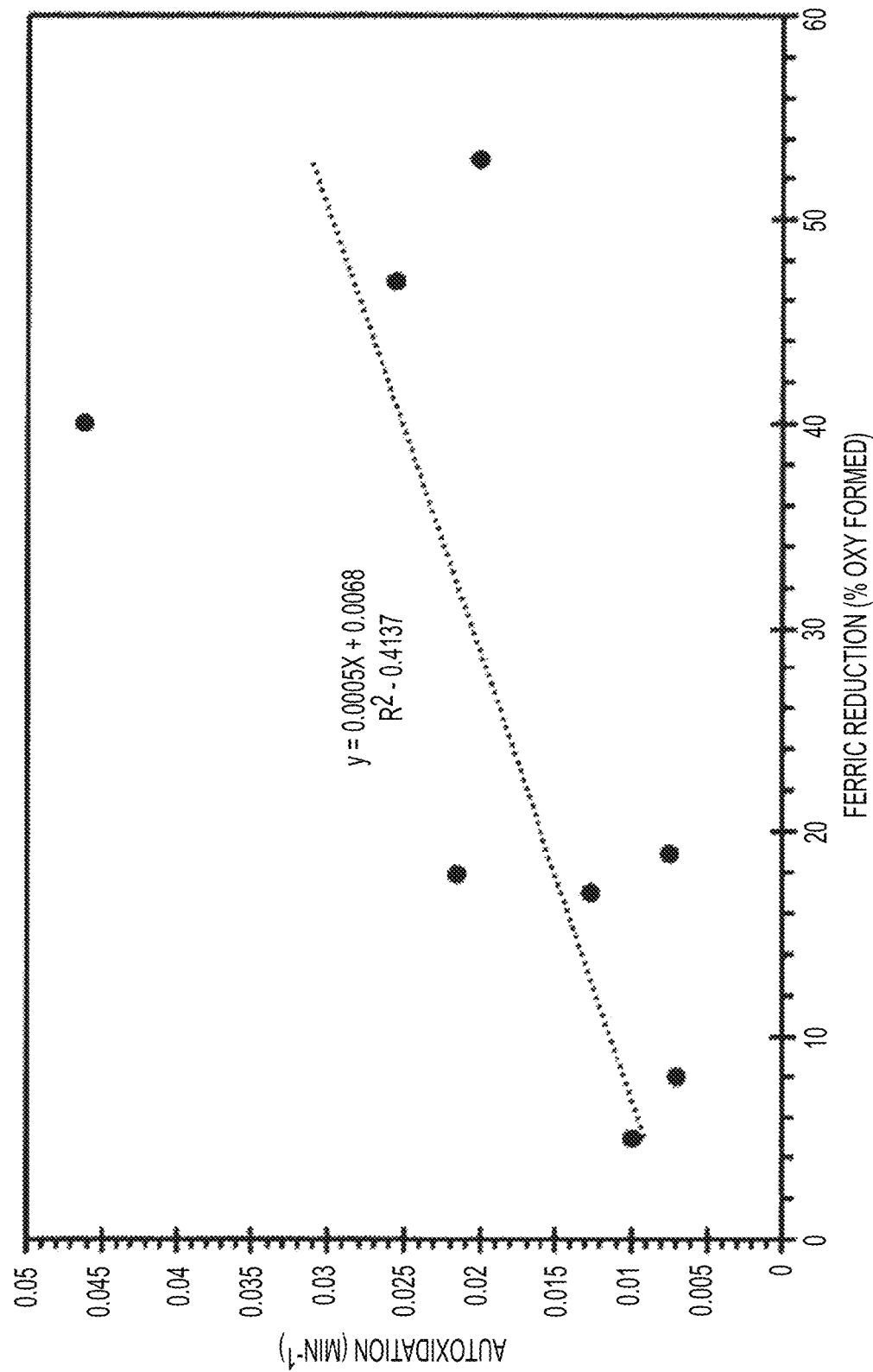
FIG. 13 illustrates the low correlation between autoxidation (ferrous to ferric-met) and ascorbate reduction (ferric-met to ferrous) for recombinant HbA proteins.
Figure 14:
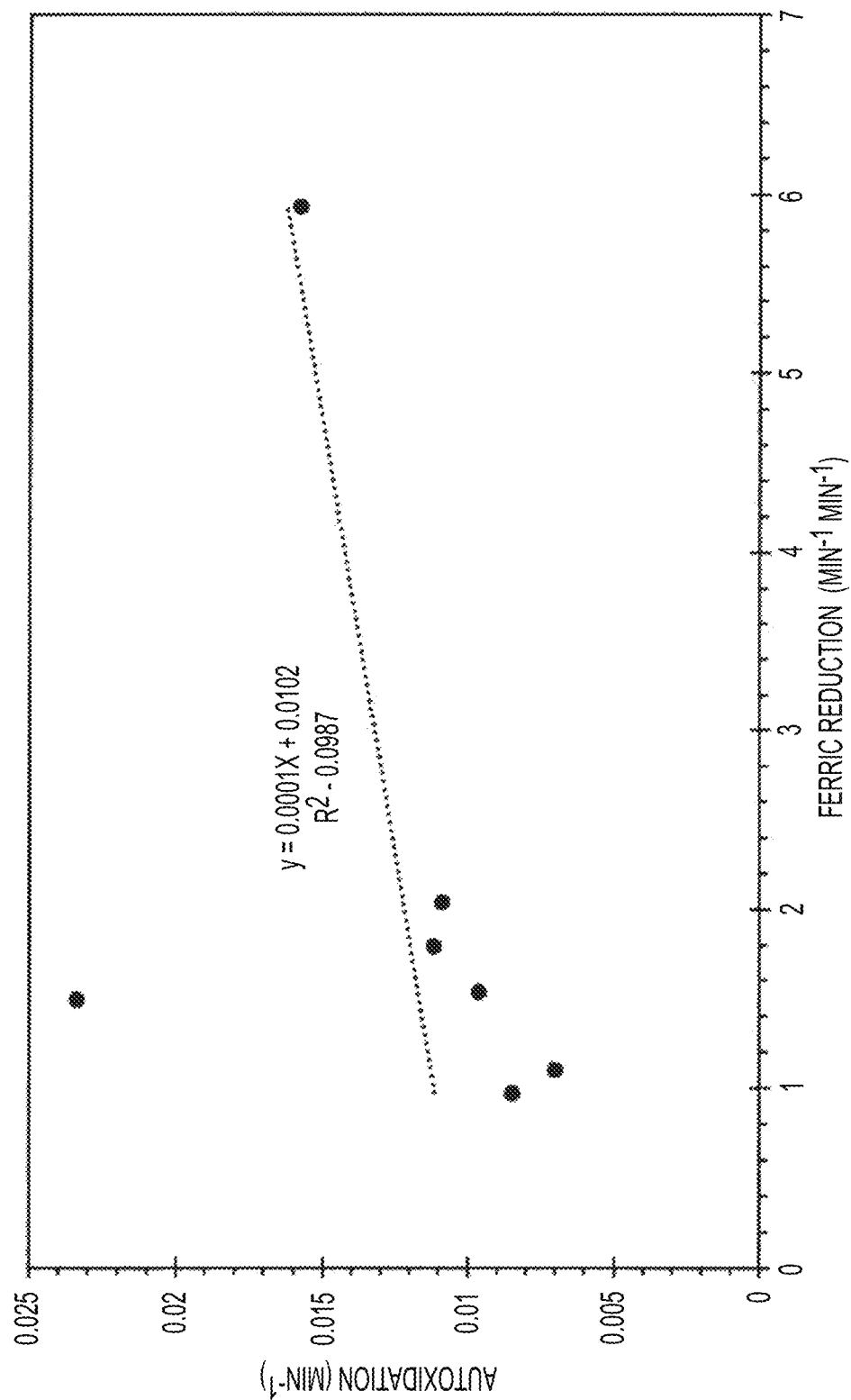
FIG. 14 illustrates the lack of a correlation between autoxidation (ferrous to ferric-met) and ascorbate reduction (ferric-met to ferrous) for recombinant HbF proteins.

The kinetic and thermodynamic stability of the ferrous-oxy state can be measured by the spontaneous oxidation (autoxidation) of the ferrous-oxy state to the ferric-met state. However, this stability does not inform the ability of external reductants to re-convert that ferric-met state back to the functional ferrous-oxy state, which is largely a function of kinetic limitations that are not easy to predict a priori. Thus, it is to be understood herein that there is a difference between modifications that aim to stabilise the ferrous form (e.g. by preventing autoxidation) and those that aim to enhance reduction of the ferric form to the ferrous by external reductants. In other words, autoxidation does not predict, nor does it correlate with, reduction of ferric to ferrous ions. As shown herein, there is a lack of correlation between autoxidation (ferrous to ferric-met) and ascorbate reduction (ferric-met to ferrous) for both recombinant HbA proteins (FIG. 13) and recombinant HbF proteins (FIG. 14). Not only are the slopes of the correlation plot not significant, but they are positive. i.e. if anything those mutants with enhanced ferrous stability are, counter-intuitively, those with decreased ferric to ferrous reduction rates.

As such, the invention relates to the unexpected finding that the addition of redox-active amino acids to the oxygen-carrying proteins (such as tyrosine) may act to facilitate electron transfer and result in the rapid reduction of the at least one iron ion.

In certain embodiments, the "reference protein" is a wild-type protein as described herein. That is to say, the reference protein may be the wild-type version of the modified protein. Alternatively, the reference protein may comprise one or more further modifications compared to the wild-type protein.

For example, the reference protein may contain at least 1, 2, 3, 4, 5, 6, 7, 8, 9, 10 or more amino acid substitutions, deletions or insertions as compared to a wild-type oxygen-carrying polypeptide sequence.

Substitutions may be naturally occurring or non-naturally occurring. In certain embodiments, the reference protein may comprise a modification which substitutes the first (N-terminal) amino acid residue substituted with a methionine. For example, the reference protein may be a human haemoglobin beta chain subunit in which the first amino acid residue (valine) of a wild-type human haemoglobin beta chain subunit has been substituted with a methionine as set forth in SEQ ID NO: 5 (also referred to as βV1M).

In certain embodiments, the reference protein may be a human haemoglobin alpha chain subunit wherein the first amino acid residue (valine) of a wild-type human haemoglobin alpha chain subunit has been substituted with a methionine as set forth in SEQ ID NO: 6 (also referred to as αV1M).

In certain embodiments, the reference protein may be a human haemoglobin gamma 1 chain subunit in which the first amino acid residue (glycine) of the wild-type human haemoglobin gamma 1 chain subunit has been substituted with a methionine as set forth in SEQ ID NO: 7 (also referred to as γ1G1M).

In certain embodiments, the reference protein may be a human haemoglobin gamma 2 chain subunit in which the first amino acid residue (glycine) of the wild-type human haemoglobin gamma 2 chain subunit has been substituted with a methionine as set forth in SEQ ID NO: 8 (also referred to as γ2G1M).

The modifications described above may help with recombinant expression, purification and/or isolation of a protein.

Throughout this specification, the conventional one letter and three letter codes for naturally occurring amino acids are used, as well as generally accepted three letter codes for other amino acids.

Thus, in an aspect of the present invention, there is provided a modified oxygen-carrying protein comprising at least one modification, wherein said modification introduces or enhances reduction of at least one metallic ion and increases a rate at which an oxidised form of the modified oxygen-carrying protein is capable of re-oxygenation to an oxygen-binding form as compared to a reference protein.

In certain embodiments, the at least one metallic ion is associated with the modified protein and the at least one metallic ion is reduced to a divalent ion. In certain embodiments, the at least one metallic ion is an iron ion and the modified protein exhibits enhanced reduction of the iron ion to $Fe^{2+}$ as compared to a reference protein.

Thus, in certain embodiments, the modified protein comprises a modification which increases the rate at which an oxidised form of the modified protein re-oxygenates to an oxygen binding form of the protein. This increase is as compared to a reference protein which does not contain the modification. A non-oxygen binding form of the modified protein may be for example a modified protein which comprises or is associated with a metallic ion in an oxidised form. In certain embodiments, the oxygen-binding form of the modified protein is a protein which is capable of binding oxygen and which may comprise or be associated with a metallic ion in a reduced form.

In certain embodiments, the modified protein is a haemoglobin and the modification increases the rate at which the protein is capable of re-oxygenating from a deoxy-haemoglobin to an oxy-haemoglobin protein.

The term "associated with" as used herein refers to an interaction between two or more molecules wherein the molecules are bound together, indirectly bound together or partially bound to each other. For example, a metallic ion may be bound by a cofactor of a protein such as a porphyrin group, the cofactor being subsequently bound by the protein, thus the metallic ion is associated with the protein. In certain embodiments, a metallic ion may be partially bound by one or more amino acid residues of the protein in addition to being bound by one or more chemical groups of a cofactor and so considered associated with the protein.

As used herein the terms "bound", "bind" and "bonding" may relate to any form of attractive interaction that may occur between two or more molecules. Non-limiting examples of binding are Van Der Waals interactions, Dipole to Dipole interactions, hydrophobic interactions, Hydrogen bonding, electrostatic bonding, covalent bonding, metallic bonding and ionic bonding.

In certain embodiments, the modified protein is an isolated protein.

The term "isolated" as used herein refers to a polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In certain embodiments, the polypeptide is purified:

(1) to a degree sufficient to obtain at least 15 residues of N-terminal or internal amino acid sequence by use of a spinning cup sequenator; or (2) to homogeneity by SDS-PAGE under non-reducing or reducing conditions using Coomassie blue or silver stain.

Isolated polypeptides include polypeptides in situ within recombinant cells, since at least one component of the oxygen-carrying polypeptide natural environment will not be present. Ordinarily, however, isolated polypeptides will be prepared by at least one purification step.

In certain embodiments, the at least one metallic ion is located within at least one porphyrin molecule bound to the modified protein.

As used herein the term "porphyrin" refers to a rigid square planar molecule made up of four five membered rings which may be made up of carbon atoms and at least one nitrogen atom. These rings may be referred to as pyrroles and are connected by methine bridges to form a larger heterocyclic ring structure with a central cavity. At least one nitrogen atom of each pyrrole ring is positioned so as to face the central cavity of the larger ring structure enabling the molecule to coordinate a metal ion in the central cavity of the heterocyclic ring structure, forming an organometallic complex.

In certain embodiments, the at least one metallic ion is at least one iron ion.

In certain embodiments, the at least one metallic ion is at least one ferric ($Fe^{3+}$) ion. Thus in certain embodiments the at least one modification may introduce or enhance the reduction of at least one ferric ion coordinated within at least one porphyrin molecule to at least one ferrous ($Fe^{2+}$) ion.

In certain embodiments, the at least one porphyrin is a haem. As used herein the terms "haem" and "heme" refer to a type of porphyrin molecule wherein the metal ion coordinated within the central cavity of the heterocyclic ring is an iron ion. In certain embodiments, the iron ion is covalently coordinated.

In certain embodiments, the at least one haem is haem B. In certain embodiments, the haem is at least one or more of haem A, haem C, haem O, haem l, haem m, haem D and/or haem S. Other suitable naturally occurring and non-naturally occurring porphyrins and haems will be known to those skilled in the art.

In certain embodiments, the modified protein comprises a globin protein. In these embodiments, the reference protein may be a naturally occurring or non-naturally occurring globin protein. As used herein the terms "globin protein" and "globin-like proteins" refers to proteins which are members of the globin protein family, wherein the protein comprises a globin fold which is made up of eight alpha helical segments. Globins are haem-containing proteins involved in the transport of oxygen. Examples of globin proteins include but are not limited to haemoglobin, myoglobin, neuroglobin, cytoglobin, erythrocruorin, leghaemoglobin, non-symbiotic haemoglobin, flavohaemoglobins, globin-coupled sensors, protoglobin and truncated 2/2 globin. Other globin and globin-like proteins will be known to those skilled in the art.

In certain embodiments, the modified protein comprises a haemoglobin. In these embodiments, the reference protein may be a naturally occurring or non-naturally occurring haemoglobin protein from the same species. Haemoglobins are tetrameric proteins made up of four polypeptide subunits each of which comprise a haem molecule. Haemoglobins constitute the oxygen carrying component of blood contained within red blood cells. As blood circulates through the lungs, the oxygen present in the alveolar capillaries diffuses through the alveolar membrane and acts to convert haemoglobin within the red blood cells to a reversible molecular complex known as oxy-haemoglobin. Because the association of the oxygen and haemoglobin is reversible, the oxygen molecules are gradually released from the haemoglobin when blood reaches the tissue capillaries. Eventually, the oxygen molecules diffuse into the tissues and is consumed by metabolism. As the oxygen is released, oxy-haemoglobin reduces to haemoglobin.

In certain embodiments, the modified protein is a vertebrate haemoglobin. In certain embodiments, the haemoglobin is a mammalian haemoglobin. In certain embodiments, the haemoglobin is a human haemoglobin. In certain embodiments, the haemoglobin is an adult haemoglobin. Aptly a human adult haemoglobin. In certain embodiments, the haemoglobin is a foetal haemoglobin. Aptly a human foetal haemoglobin. Non-limiting examples of naturally occurring human haemoglobins are given in Table 1. The most common form of haemoglobin found in humans is $\alpha_2\beta_2$ (also referred to as adult haemoglobin) i.e. it is composed of two alpha chain subunits and two beta chain subunits. An example of foetal haemoglobin is $\alpha_2\gamma_2$ (i.e. it is composed of two alpha chain subunits and two gamma chain subunits).

TABLE 1

Types of human haemoglobins

| Name | Subunits |
|---|---|
| Gower 1 | $\zeta_2\epsilon_2$ |
| Gower 2 | $\alpha_2\epsilon_2$ |
| Haemoglobin Portland I | $\zeta_2\gamma1_2$ or $\zeta_2\gamma2_2$ |
| Haemoglobin Portland II | $\zeta_2\beta_2$ |
| Haemoglobin F | $\alpha_2\gamma1_2$ or $\alpha_2\gamma2_2$ |
| Haemoglobin A | $\alpha_2\beta_2$ |
| Haemoglobin $A_2$ | $\alpha_2\delta_2$ |
| Haemoglobin H | $\beta_4$ |
| Haemoglobin Barts | $\gamma_4$ |

In certain embodiments, the haemoglobins listed in Table 1 are reference proteins as referred to herein.

In certain embodiments, the modified protein comprises at least one haemoglobin chain subunit. In certain embodiments, the modified protein is a haemoglobin chain subunit. In certain embodiments, the haemoglobin subunit is a member of the beta chain superfamily.

As defined herein the term "superfamily" refers to proteins that may have low sequence identities but whose structural and functional features suggest that the proteins share a common evolutionary origin. By way of example the subunit may be selected from at least one of beta, alpha, gamma 1, gamma 2, delta, zeta or epsilon haemoglobin chain subunits.

In certain embodiments, the modified protein is a human haemoglobin beta chain subunit. In certain embodiments, the modified protein is a human haemoglobin alpha chain subunit. In certain embodiments, the modified protein is a human haemoglobin gamma chain subunit. In certain embodiments, the modified protein is a human haemoglobin gamma 1 chain subunit. In certain embodiments, the modified protein is a human haemoglobin gamma 2 chain subunit.

In certain embodiments, the modified protein may be a haemoglobin beta chain subunit homologue. In certain embodiments, the modified protein may be a homologue of a haemoglobin gamma chain subunit. In certain embodiments, the modified protein may be a homologue of a haemoglobin alpha chain subunit. As used herein the term "homologous proteins" and "homologue" refer to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST. Using this information, protein sequences can be grouped. A phylogenetic tree can be built using the amino acid sequences. Amino acid sequences can be entered in a program such as the Vector NTI Advance suite and a Guide Tree can be created using the Neighbor Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Understanding the homology between molecules can help reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions.

In certain embodiments, the modified protein is an ortholog of a haemoglobin beta chain subunit. In certain embodiments, the modified protein is an ortholog of a haemoglobin gamma chain subunit. In certain embodiments, the modified protein is an ortholog of a haemoglobin alpha chain subunit.

Typically, greater than 30% amino acid sequence identity between two polypeptides (preferably, over a specified region) is considered to be an indication of functional equivalence and thus an indication that two or more proteins are homologous.

In certain embodiments, proteins that are homologues of the human haemoglobin beta chain subunit have a degree of sequence identity with the wild-type human haemoglobin beta subunit sequence of SEQ ID NO: 1 of greater than 30%. In other embodiments, homologues have degrees of identity of greater than 70%, 80%, 90%, 95%, 98% or 99%, respectively with the protein sequence of SEQ ID NO: 1.

In certain embodiments, proteins that are homologues of the human haemoglobin alpha chain subunit have a degree of sequence identity with the wild-type human haemoglobin alpha subunit sequence of SEQ ID NO: 2 of greater than 30%. In other embodiments, homologues have degrees of identity of greater than 70%, 80%, 90%, 95%, 98% or 99%, respectively with the protein sequence of SEQ ID NO: 2.

In certain embodiments, proteins that are homologues of the human haemoglobin gamma chain subunit 1 or gamma chain subunit 2 have a degree of sequence identity with the wild-type human haemoglobin gamma subunit 1 or gamma chain subunit 2 sequences of SEQ ID NO: 3 and SEQ ID NO: 4 respectively, of greater than 30%. In other embodiments, homologues have degrees of identity of greater than 70%, 80%, 90%, 95%, 98% or 99%, respectively with the protein sequences of SEQ ID NO: 3 or SEQ ID NO: 4.

"Percent (%) amino acid sequence identity" as used herein is defined as the percentage of amino acid residues in a candidate sequence that are identical with the amino acid residues in a specific modified oxygen-carrying protein, after aligning the sequences and introducing gaps, if necessary, to achieve the maximum percent sequence identity, and not considering any conservative substitutions as part of the sequence identity.

Alignment for purposes of determining percent amino acid sequence identity can be achieved in various ways that are within the skill in the art, for instance, using publicly available computer software such as BLAST, BLAST-2, ALIGN or ClustalW software. Those skilled in the art can determine appropriate parameters for measuring alignment, including any algorithms needed to achieve maximal alignment over the full length of the sequences being compared.

Thus in certain aspects of the present invention there is provided a modified haemoglobin chain subunit wherein the modification introduces or enhances, as compared to a reference haemoglobin chain subunit, reduction of at least one iron ion associated with the modified haemoglobin chain subunit to a ferric ($Fe^{2+}$) ion. In certain embodiments, the haemoglobin chain subunit is haemoglobin beta chain subunit. In certain embodiments, the haemoglobin beta chain subunit is a human haemoglobin beta chain subunit. In certain embodiments, the haemoglobin chain subunit is haemoglobin alpha chain subunit. In certain embodiments, the haemoglobin alpha chain subunit is a human haemoglobin alpha chain subunit. In certain embodiments, the haemoglobin chain subunit is haemoglobin gamma chain subunit. In certain embodiments, the haemoglobin gamma chain subunit is a human haemoglobin gamma chain subunit.

In certain embodiments, the modified protein comprises at least one human haemoglobin beta chain subunit wherein the at least one modification is βT84Y. In certain embodiments, the at least one modification is βF85Y. In certain embodiments, the at least one modification is βL96Y.

In certain embodiments, the modified protein comprises at least one human haemoglobin beta chain subunit wherein the at least one modification is a plurality of modifications selected from one or more of βT84Y, βF85Y and/or βL96Y or a combination thereof.

In certain embodiments, the modified protein comprises at least one human haemoglobin alpha chain subunit wherein the at least one modification is αL91Y. In certain embodiments, the at least one modification is αL29F.

In certain embodiments, the modified protein comprises at least one human haemoglobin alpha chain subunit wherein the at least one modification is a plurality of modifications selected from one or more of αL91Y and/or αL29F or a combination thereof.

In certain embodiments, the modified protein comprises at least one human haemoglobin gamma 1 chain subunit wherein the at least one modification is γ1V67F. In certain embodiments, the at least one modification is γ1L96Y.

In certain embodiments, the modified protein comprises at least one human haemoglobin gamma 1 chain subunit wherein the at least one modification is a plurality of modifications selected from one or more γ1V67F and γ1L96Y or a combination thereof.

In certain embodiment, the modified protein comprises at least one human haemoglobin gamma 2 chain subunit wherein the at least one modification is γ2V67F. In certain embodiments, the at least one modification is γ2L96Y.

In certain embodiment, the modified protein comprises at least one human haemoglobin gamma 2 chain subunit wherein the at least one modification is a plurality of modifications selected from one or more γ2V67F and γ2L96Y or a combination thereof.

In certain embodiments, the modified protein may comprise at least one further modification as compared to a reference protein e.g. a wild-type oxygen-carrying protein. By way of example the modified protein may comprise one, two three, four, five, six or more additional amino acid residue substitutions, deletions and/or insertions (which may be contiguous or non-contiguous). These further modifications may affect further properties of the modified protein such as oxygen affinity or cooperativity, stability and assembly rate, decreased porphyrin loss, decreased metallic ion autoxidation rate, resistance to proteolytic degradation, decreased aggregation, nitric oxide reactivity and nitric oxide binding, production and purification means and solubility. Such modifications will be known by those skilled in the art and may be incorporated into the modified proteins of embodiments of the present invention.

In certain embodiments, the modified proteins of the present invention may include at least one further modification such as but not limited to those disclosed WO2009/004309 which is incorporated herein by reference. Without being bound by theory such further modifications may introduce or enhance reduction of at least one tetravalent cation to a trivalent cation as compared to a reference protein. For example, the reduction of a ferryl ($Fe^{4+}$) ion to a ferric ($Fe^{3+}$) ion as is disclosed in WO2009/004309. In these embodiments, the modified protein may have decreased toxicity as compared to a reference protein.

In certain embodiments, the modified proteins of the present invention may include at least one further modification such as but not limited to a substitution of the most N-terminal amino acid residue with a methionine residue.

In certain embodiments, the modified protein further comprises at least one further modification which reduces nitric oxide reactivity of the modified protein.

In certain embodiments, the modified protein further comprises a plurality of further modifications.

In certain embodiments, the modified protein is a human haemoglobin beta chain subunit and may comprises one or more further modifications listed below: NA1(Val>Met); B13(Leu>Phe or Trp); G12(Leu>Phe or Trp); B10 (Leu>Phe) and E4(Val>Leu); B10(Leu>Trp) and E4(Val>Leu); B14(Leu>Phe or Trp); G8(Leu>Phe) and G12 (Leu>Trp); E11 (Val>Leu) and G8(Leu>Trp); E11 (Val>Trp) and G8(Leu>Met); E11 (Val>Leu) and G8(Leu>Phe); E11 (Val>Leu) and G8(Leu>Met); E11 (Val>Phe) and G8(Leu>Ile); E11(Val>Phe) and G8(Leu>Phe); E11(Val>Phe) and G8(Leu>Trp); E11 (Val>Phe) and G8(Leu>Met); E11 (Val>Met) and G8(Leu>Trp); E11 (Val>Met) and G8(Leu>Trp) and E7(His>Gln); E11 (Val>Trp) and G8(Leu>11e); E7(His>Gln) and E11(Val>Trp); E7(His>Gln) and E11 (Val>Leu); E7(His>Gln) and E11 (Val>Phe); E7(His>Gln) and E11 (Val>Phe) and G8(Leu>Phe or Trp); E7(His>Gln)

and E11(Val>Leu or Trp) and G8(Leu>Phe or Trp); E11 (Val>Trp or Phe) and G12(Leu>Trp or Met); E11(Val>Trp or Phe) and B13(Leu>Trp or Met); B10(Leu>Trp) and B13(Leu>Trp or Met); B10(Leu>Phe) and B13(Leu>Trp); B10(Leu>Trp or Phe) and G12(Leu>Trp); B10(Leu>Phe) and G12(Leu>Met); G8(Leu>Trp) and G12(Leu>Trp or Met); or G8(Leu>Trp) and B13(Leu>Trp or Met); C7 (Phe>Tyr).

The numbering used above is based on helix chain numbering, which can be cross-referenced to the primary sequence numbering of Table 2 below for the human haemoglobin $A_o$ beta and alpha chain subunits. It will be understood by those skilled in the art that haemoglobin subunit proteins may be numbered by reference to individual helices or inter-helix residues as is set out in Table 2. For example, the F1 residue of the human haemoglobin beta chain subunit may be equivalent to the F1 residue in other haemoglobin beta chain subunits. It will be understood by those skilled in the art that at least one or more of the further modifications at equivalent positions in other modified proteins of the present invention may also be included.

In certain embodiments of the present invention the modified protein comprises at least one conservative amino acid substitution as compared to a native oxygen-carrying protein. For examples, the modified protein may contain no more than 2, 3, 4, 5, 6, 7, 8, 9, or 10 conservative amino acid substitutions as compared to a native oxygen-carrying polypeptide sequence. The term "conservative substitution" as used herein refers to substitutions of amino acid residues of an oxygen carrying protein that have no effect on activity or properties of the oxygen-carrying protein. Conservative substitutions may be naturally occurring or non-naturally occurring.

In certain embodiments, the at least one modification introduces or enhances, as compared to a reference protein, the transfer of at least one electron between at least one amino acid residue of the modified protein and the at least one metallic ion associated with the modified protein.

Thus, in certain embodiments the at least one modification introduces or enhances the transfer of at least one electron to the at least one metallic ion via at least one amino acid residue of the protein. In certain embodiments, the at least one metallic ion is a ferric ion.

In certain embodiments, the at least one modification comprises an insertion of at least one redox-active amino acid.

In certain embodiments, the at least one modification comprises a substitution of an amino acid residue of a reference protein with at least one redox-active amino acid residue.

In certain embodiments, the at least one modification comprises an insertion of at least one redox-active amino acid residue and/or at least one substitution of an amino acid residue of a reference protein with at least one redox-active amino acid residue.

As used herein the term "redox-active" amino acid is a naturally occurring or non-naturally occurring amino acid residue that is able to undergo at least one reduction and/or oxidation reaction and thus is able to donate or accept at least one electron.

In certain embodiments, the at least one redox-active amino acid residue is located at a distance of at most about 20 Å from the at least one metallic ion. By way of example the at least one redox-active amino acid is located 1 Å, 2 Å, 3 Å, 4 Å, 5 Å, 6 Å, 7 Å, 8 Å, 9 Å, 10 Å, 11 Å, 12 Å, 13 Å, 14 Å, 15 Å, 16 Å, 17 Å, 18 Å, 19 Å or 20 Å from the at least one metallic ion associated with the modified protein. The redox-active amino acid may be located so as to be able to donate at least one electron to the at least one metallic ion.

In certain embodiments, the at least one redox-active amino acid is located so as to be surface accessible. The term "surface accessible" as used herein refers to an amino acid residue of a protein which is located so as to be able to take part in reactions at the surface of a protein. By way of example the amino acid residue is located so as to be able to accept at least one electron from an external electron donor (i.e. a reductant).

In certain embodiments, the at least one redox-active amino is surface accessible and located at a distance of up to 20 Å from the at least one metallic ion.

In certain embodiments, the at least one redox-active amino acid is located at most about 20 Å from an outer boundary of at least one haem group. By way of example the at least one redox-active amino acid is located 1 Å, 2 Å, 3 Å, 4 Å, 5 Å, 6 Å, 7 Å, 8 Å, 9 Å, 10 Å, 11 Å, 12 Å, 13 Å, 14 Å, 15 Å, 16 Å, 17 Å, 18 Å, 19 Å or 20 Å from an outer boundary of at least one haem group. In certain embodiments, the at least one redox-active amino acid is located about 10 Å from an outer boundary of at least one group. As used herein the term "outer boundary" refers to an imaginary perimeter formed between the outer most chemical groups of a molecule, such as a haem group.

In certain embodiments, the at least one redox-active amino is surface accessible and located at a distance of up to 20 Å from the outer boundary of a haem group.

In certain embodiments, the at least one redox-active amino acid residue is at least one or more of tyrosine, histidine, phenylalanine and/or tryptophan. Other suitable redox-active amino acid residues will be known to those skilled in the art.

In certain embodiments, the at least one redox-active amino acid residue is tyrosine.

In certain embodiments, the at least one redox-active amino acid residue is phenylalanine.

Without being bound by theory in certain embodiments the at least one modification introduces or enhances an electron transfer pathway to the at least one metallic ion associated with the modified protein via the at least one redox-active amino acid residue of the modified protein. This electron transfer pathway via the redox-active amino acid residue of the modified protein may have a higher affinity than a direct electron transfer pathway to the at least one metallic ion and so can result in more rapid reduction of the at least one metallic ion.

In certain embodiments, the modified protein is conjugated to at least one non-antigenic moiety. In certain embodiments, the non-antigenic moiety is conjugated to the modified protein in order to help improve solubility and/or half-life in vivo (e.g. in plasma) and/or bioavailability. Such conjugates may also help to reduce clearance (e.g. renal clearance) of proteins. As used herein the term "conjugated" refers to a physical attachment of one identifiable moiety to another. A number of suitable non-antigenic moieties will be known by those skilled in the art.

In certain embodiments, the moiety may be a protein. In certain embodiments, wherein the moiety is a protein, the protein moiety may be produced as a fusion protein with the modified protein. Alternatively, the protein moiety and the modified protein may be expressed separately or co-expressed and linked by chemical means such as by a chemical cross linker. Suitable chemical cross linkers will be known by those skilled in the art. By way of example cross linking agents may be one or more of glutaraldehyde, disparin derivatives, polyaldehydes, diphosphate esters, triphosphate esters.

In certain embodiments, the protein moiety is an antioxidant enzyme. By way of example the antioxidant enzyme may be a catalase and/or superoxide dismutase. In certain embodiments, the protein moiety is a human catalase and/or human superoxide dismutase.

In certain embodiments, the at least one non-antigenic moiety is at least one polymeric moiety. In certain embodiments, the polymeric moiety is water-soluble, non-toxic and pharmaceutically inert. In certain embodiments, the polymeric moiety is at least one polyalkylene glycol. In certain embodiments, the polymeric moiety is polyethylene glycol (PEG).

In certain embodiments, the polymeric moiety can be covalently bound through amino acid residues via a reactive group, such as, a free amino, carboxyl group or sulfhydryl group. Reactive groups are those to which an activated PEG molecule can be bound. Examples of naturally occurring amino acid residues having a free amino group include lysine residues and the N-terminal amino acid residues; those having a free carboxyl group include aspartic acid residues glutamic acid residues and the C-terminal amino acid residue. Sulfhydryl groups (e.g., on cysteine) can also be used as a reactive group for attaching for example polyethylene glycol molecules.

The polymeric moiety used can be of any molecular weight, and can be branched or unbranched. In certain embodiments, the polyalkylene glycol has a molecular weight between about 1000 Daltons and about 100,000 Da (the term "about" indicating that in preparations of polyalkylene glycols, some molecules will weigh more, some less, than the stated molecular weight). For example, the polyalkylene glycol can have an average molecular weight of about 1000, 5000, 10000, 15000, 20000, 25000, 30000, 35000, 40000, 50000, 60000, 70000, 80000, 90000 or 100000 Da.

The number of polymeric moieties attached to each modified protein (i.e. number of PEG molecules) can also vary. For example, the modified protein may be linked, on average, to 1, 2, 3, 4, or 5, or more polyethylene glycol molecules.

In certain embodiments of the present invention there is provided a multimeric protein comprising at least one modified protein of the present disclosure. In certain embodiments, multimeric forms of the modified protein may prolong circulation life time of the modified protein, improve a rate at which an oxidised form of the modified oxygen-carrying protein is capable of re-oxygenation to an oxygen-binding form as compared to a reference protein, improve oxygen-carrying properties and/or reduce side-effects.

In certain embodiments, the modified protein is a dimer. In certain embodiments, the modified protein is a trimer. In certain embodiments, the modified protein is a tetramer.

In certain embodiments, the multimeric protein comprises at least one or more reference oxygen-carrying proteins and/or reference oxygen-carrying protein subunits. In certain embodiments, the at least one reference oxygen-carrying protein and/or reference oxygen-carrying protein subunit may include at least one further modification as described herein.

These further modifications may affect properties of each of the at least one reference oxygen-carrying proteins and/or reference oxygen-carrying protein subunits such as oxygen affinity or cooperativity, stability and assembly rate, decreased porphyrin loss, decreased metallic ion autoxidation rate, resistance to proteolytic degradation, decreased aggregation, nitric oxide reactivity and nitric oxide binding, production and purification means and solubility. Such modifications will be known by those skilled in the art.

By way of example further modifications that may be included wherein the in the at least one reference oxygen-carrying protein and/or oxygen-carrying protein subunit comprises a haemoglobin alpha chain subunit may include: NA1(Val>Met); E11(Val>Leu) and E7(His>Gln); E11 (Val>Phe or Trp) and E7(His>Gln); E11(Val>Phe or Trp or Leu) and E7(His>Gln) and G8(Leu>Phe or Trp); B10 (Leu>Phe) and E4(Val>Leu); 0 B10(Leu>Trp) and E4(Val>Leu); B10(Leu>Trp) and E7(His>Gln); B10 (Leu>Trp) and E11(Val>Phe); B10(Leu>Trp) and E11 (Val>Trp); B10(Leu>Trp) and E11(Val>Leu) and G8(Leu>Trp); B10(Leu>Trp) and E11 (Val>Leu) and G8(Leu>Phe); B10(Leu>Trp) and E11(Val>Phe) and G8(Leu>Trp); B10(Leu>Trp) and E11(Val>Phe) and G8(Leu>Ilc); B10(Leu>Trp) and E7(His>Gln) and E11 (Val>Leu) and G8(Leu>Trp); B10(Leu>Trp) and E11 (Val>Trp) and G8(Leu>Trp); E11 (Val>Leu) and G8(Leu>Phe); E11 (Val>Leu) and G8(Leu>Trp); B13 (Met>Phe or Trp); G12(Leu>Phe or Trp); or B14(Phe>Trp).

The numbering used above is based on helix chain numbering, which can be cross-referenced to the primary sequence numbering of Table 2 below for the human haemoglobin beta and alpha chain subunits. It will be understood by those skilled in the art that at least one or more of these further modifications at equivalent positions in other oxygen-carrying proteins of the may also be included.

Thus in certain embodiments wherein the modified protein of the present invention is a haemoglobin beta chain subunit the multimeric protein may comprise a tetrameric haemoglobin protein comprising two haemoglobin beta chain subunits of embodiments of the present invention and two wild-type haemoglobin alpha chain subunits or two reference alpha chain subunits e.g. αV1M haemoglobin alpha chain subunits. In certain embodiments, the multimeric protein may comprise any number or combination of modified proteins as described herein and any number or combination of reference proteins (e.g. haemoglobin chain subunits including the further modifications V1M and G1M and/or wild-type haemoglobin chain subunits) as described herein. For example, the multimer may be any one of the tetrameric haemoglobins given in Table 1 wherein at least one chain subunit is a modified protein as described herein.

In certain embodiments, the modified protein is adult haemoglobin (also referred to as Haemoglobin A, HbA, or $\alpha_2\beta_2$) comprising 2 alpha chain subunits and two beta chain subunits.

In certain embodiments, wherein the modified protein is a multimer, one or more modifications and/or further modifications as described herein may be located in a single subunit or may be distributed through two, three or four different subunits. For example, a multimer may include a haemoglobin alpha chain subunit comprising the modifications αL91Y and αL29F and the further modification αV1M and a second haemoglobin alpha chain subunit that is a wild-type human alpha chain subunit. In an alternative embodiment, a multimer may comprise a haemoglobin alpha chain subunit comprising the modification αL91Y and the further modification αV1M and a second haemoglobin alpha chain subunit comprising the modifications αL91Y and αL29F and the further modification αV1M. Any number or combination of modifications and/or further modifications as described herein may be included within any number of multimer subunits.

In certain embodiments, the modified protein is a foetal haemoglobin (also referred to as haemoglobin F, HbF, and/or $\alpha_2\gamma_2$). Foetal haemoglobin comprises 2 alpha chain subunits and 2 gamma chain subunits. Aptly the gamma chain subunits may be gamma 1 or gamma 2.

In certain embodiments, the modified protein comprises a foetal haemoglobin comprising at least one haemoglobin alpha chain subunit comprising one or more modifications selected from αL91Y and αL29F or a combination thereof.

In certain embodiments, the modified protein comprises a foetal haemoglobin comprising at least one haemoglobin gamma1 and/or gamma 2 chain subunit comprising one or more modifications selected from γL96Y and γV67F or a combination thereof.

In certain embodiments, the modified protein comprises a foetal haemoglobin wherein the at least one modification is αL91Y.

In certain embodiments, the modified protein comprises a foetal haemoglobin comprising the at least one modification, αL91Y, and a further modification selected from αV1M and/or γG1M or a combination thereof.

In certain embodiments, the modified protein comprises a foetal haemoglobin comprising the at least one modification γL96Y and a further modification selected from αV1M and/or γG1M or a combination thereof.

In certain embodiments, the modified protein comprises a foetal haemoglobin comprising the modifications, αL91Y and γL96Y and a further modification selected from αV1M and γG1M or a combination thereof.

In certain embodiments, the modified protein comprises a foetal haemoglobin comprising the modifications αL29F, γV67F and γL96Y or a combination thereof and a further modification selected from αV1M and γG1M or a combination thereof.

In certain embodiments, the modified protein comprises a foetal haemoglobin comprising the modifications αL29F, αL91Y, γV67F and γL96Y or a combination thereof and the further modifications αV1M and γG1M or a combination thereof.

Aptly the haemoglobin alpha chain subunit is a human haemoglobin alpha chain subunit.

Aptly the haemoglobin gamma chain subunit is a human haemoglobin gamma chain subunit.

Aptly the foetal haemoglobin comprises at least one human gamma 1 chain subunit and/or human gamma 2 chain subunit.

In certain embodiments, the modified protein comprises at least one human haemoglobin alpha chain subunit as set forth in SEQ ID NO: 12 (αL91Y modified alpha chain subunit) and at least one human haemoglobin gamma 2 chain subunit as set forth in SEQ ID NO: 4 (wild-type human haemoglobin gamma 2 chain subunit). Aptly the modified protein comprises two human haemoglobin alpha chain subunits as set forth in SEQ ID NO: 12 (αL91Y modified alpha chain subunit) and two human haemoglobin gamma 2 chain subunit as set forth in SEQ ID NO: 4 (wild-type human haemoglobin gamma 2 chain subunit).

In certain embodiments, the modified protein comprises at least one human haemoglobin alpha chain subunit as set forth in SEQ ID NO: 6 (αV1M reference) and at least one human haemoglobin gamma 2 chain subunit as set forth in SEQ ID NO: 13 (γL96Y modified γG1M). Aptly the modified protein comprises two human haemoglobin alpha chain subunits as set forth in SEQ ID NO: 12 (αL91Y modified) and two human haemoglobin gamma 2 chain subunit as set forth in SEQ ID NO: 13 (γL96Y modified γG1M).

In certain embodiments, the modified protein comprises at least one human haemoglobin alpha chain subunits as set forth in SEQ ID NO: 11 (αL91Y modified, V1M) and at least one human haemoglobin gamma 2 chain subunit as set forth in SEQ ID NO: 13 (γL96Y modified γG1M). Aptly the modified protein comprises two human haemoglobin alpha chain subunits as set forth in SEQ ID NO: 11 (αL91Y modified, V1M) and two human haemoglobin gamma 2 chain subunit as set forth in SEQ ID NO: 13 (γL96Y modified γG1M).

In certain embodiments, the modified protein comprises at least one human haemoglobin alpha chain subunits as set forth in SEQ ID NO: 14 (αL29F modified αV1M) and at least one human haemoglobin gamma 2 chain subunit as set forth in SEQ ID NO: 15 (γV67F modified γG1M) and at least one human haemoglobin gamma 2 chain subunit as set forth in SEQ ID NO: 13 (γL96Y modified γG1M). Aptly the modified protein comprises two human haemoglobin alpha chain subunits as set forth in SEQ ID NO: 14 (αL29F modified αV1M) and one human haemoglobin gamma 2 chain subunit as set forth in SEQ ID NO: 15 (γV67F modified γG1M) and one human haemoglobin gamma 2 chain subunit as set forth in SEQ ID NO: 13 (γL96Y modified γG1M).

In certain embodiments, the modified protein comprises at least one human haemoglobin alpha chain subunits as set forth in SEQ ID NO: 14 (αL29F modified αV1M) and at least one human haemoglobin gamma 2 chain subunit as set forth in SEQ ID NO: 17 (γV67F, γL96Y modified γG1M). Aptly the modified protein comprises two human haemoglobin alpha chain subunits as set forth in SEQ ID NO: 14 (αL29F modified αV1M) and two human haemoglobin gamma 2 chain subunit as set forth in SEQ ID NO: 17 (γV67F, γL96Y modified γG1M).

In certain embodiments, the modified protein comprises at least one human haemoglobin alpha chain subunits as set forth in SEQ ID NO: 14 (αL29F modified αV1M) and at least one human haemoglobin alpha chain subunits as set forth in SEQ ID NO: 11 (αL91Y modified αV1M) and at least one human haemoglobin gamma 2 chain subunit as set forth in SEQ ID NO: 15 (γV67F modified γG1M) and at least one human haemoglobin gamma 2 chain subunit as set forth in SEQ ID NO: 13 (γL96Y modified γG1M). Aptly the modified protein comprises one human haemoglobin alpha chain subunits as set forth in SEQ ID NO: 14 (αL29F modified αV1M) and one human haemoglobin alpha chain subunits as set forth in SEQ ID NO: 11 (αL91Y modified αV1M) and one human haemoglobin gamma 2 chain subunit as set forth in SEQ ID NO: 15 (γV67F modified γG1M) and one human haemoglobin gamma 2 chain subunit as set forth in SEQ ID NO: 13 (γL96Y modified γG1M).

In certain embodiments, the modified protein comprises at least one human haemoglobin alpha chain subunits as set forth in SEQ ID NO: 16 (αL29F, αL91Y modified αV1M) and at least one human haemoglobin gamma 2 chain subunit as set forth in SEQ ID NO: 17 (γV67F, γL96Y modified γG1M). Aptly the modified protein comprises two human haemoglobin alpha chain subunits as set forth in SEQ ID NO: 16 (αL29F, αL91Y modified αV1M) and two human haemoglobin gamma 2 chain subunit as set forth in SEQ ID NO: 17 (γV67F, γL96Y modified γG1M).

In certain embodiments the multimer and/or multimeric protein is cross linked. Methods of cross linking proteins will be known by those skilled in the art but by way of example suitable cross linking method may include but are not limited to chemical cross lining and fusion protein recombinant expression.

Without being bound by theory in certain embodiments of the present invention wherein the modified protein is a haemoglobin or haemoglobin chain subunit the introduced or enhanced reduction activity may increase the reduction of a ferric ($Fe^{3+}$) ion of a non-functional (non-oxygen binding) met-haemoglobin form to a functional (oxygen binding) oxy-haemoglobin form wherein the iron ion is a ferrous ($Fe^{2+}$) ion. Thus the at least one modification may help to increase the rate at which an oxygen carrying and/or binding form of a haemoglobin and/or haemoglobin chain subunit is formed.

In certain embodiments, wherein the modified protein is a haemoglobin chain subunit the at least one modification is located on the EF helix.

In certain embodiments, the at least one modification is located on the F helix.

In certain embodiments, the at least one modification is located on the B10 helix.

In certain embodiments, the at least one modification is located on the E11 helix.

In certain embodiments, the at least one modification is located on the FG loop.

In certain embodiments, wherein when the modified protein is a haemoglobin chain subunit the at least one modification is residue EF8 (Thr>Tyr).

In certain embodiments, the at least one modification is helical residue F1 (Phe>Tyr).

In certain embodiments, the at least one modification is helical residue F7 (Leu>Tyr).

In certain embodiments, the at least one modification is helical residue B10 (Leu>Phe).

In certain embodiments, the at least one modification is helical residue E11 (Val>Phe).

In certain embodiments, the at least one modification is helical residue FG3 (Leu>Tyr).

In certain embodiments, the at least one modification is a plurality of modifications selected from helical residue F1 (Phe>Tyr), helical residue F7 (Leu>Tyr), helical residue B10 (Leu>Phe), helical residue E11 (Val>Phe) and/or helical residue FG3 (Leu>Tyr) or a combination thereof.

The numbering used above to define the location of certain modifications refers to the helix chain positions for human haemoglobin alpha and beta chain subunits as is give in Table 2. It will be understood by those skilled in the art that the helical residue positions may apply to other haemoglobin chain subunits and other oxygen-carrying proteins of embodiments of the present invention.

TABLE 2

| Amino Acid Sequence and Helical Residue Notation for Human Haemoglobin $A_O$ | | | | | | | |
|---|---|---|---|---|---|---|---|
| Helix | α | Helix | β | Helix | A | Helix | β |
| NA1 | 1 Val | NA1 | 1 Val | E17 | 68 Asn | E17 | 73 Asp |
| — | — | NA2 | 2 His | E18 | 69 Ala | E18 | 74 Gly |
| NA2 | 2 Leu | NA3 | 3 Leu | E19 | 70 Val | E19 | 75 Leu |
| A1 | 3 Ser | A1 | 4 Thr | E20 | 71 Ala | E20 | 76 Ala |
| A2 | 4 Pro | A2 | 5 Pro | EF1 | 72 His | EF1 | 77 His |
| A3 | 5 Ala | A3 | 6 Glu | EF2 | 73 Val | EF2 | 78 Leu |
| A4 | 6 Asp | A4 | 7 Glu | EF3 | 74 Asp | EF3 | 79 Asp |
| A5 | 7 Lys | A5 | 8 Lys | EF4 | 75 Asp | EF4 | 80 Asn |
| A6 | 8 Thr | A6 | 9 Ser | EF5 | 76 Met | EF5 | 81 Leu |
| A7 | 9 Asn | A7 | 10 Ala | EF6 | 77 Pro | EF6 | 82 Lys |
| A8 | 10 Val | A8 | 11 Val | EF7 | 78 Asn | EF7 | 83 Gly |
| A9 | 11 Lys | A9 | 12 Thr | EF8 | 79 Ala | EF8 | 84 Thr |
| A10 | 12 Ala | A10 | 13 Ala | F1 | 80 Leu | F1 | 85 Phe |
| A11 | 13 Ala | A11 | 14 Leu | F2 | 81 Ser | F2 | 86 Ala |
| A12 | 14 Trp | A12 | 15 Trp | F3 | 82 Ala | F3 | 87 Thr |
| A13 | 15 Gly | A13 | 16 Gly | F4 | 83 Leu | F4 | 88 Leu |
| A14 | 16 Lys | A14 | 17 Lys | F5 | 84 Ser | F5 | 89 Ser |
| A15 | 17 Val | A15 | 18 Val | F6 | 85 Asp | F6 | 90 Glu |
| A16 | 18 Gly | — | — | F7 | 86 Leu | F7 | 91 Leu |
| AB1 | 19 Ala | — | — | F8 | 87 His | F8 | 92 His |
| B1 | 20 His | B1 | 19 Asn | F9 | 88 Ala | F9 | 93 Cys |
| B2 | 21 Ala | B2 | 20 Val | FG1 | 89 His | FG1 | 94 Asp |
| B3 | 22 Gly | B3 | 21 Asp | FG2 | 90 Lys | FG2 | 95 Lys |
| B4 | 23 Glu | B4 | 22 Glu | FG3 | 91 Leu | FG3 | 96 Leu |
| B5 | 24 Tyr | B5 | 23 Val | FG4 | 92 Arg | GF4 | 97 His |
| B6 | 25 Gly | B6 | 24 Gly | FG5 | 93 Val | FG5 | 98 Val |
| B7 | 26 Ala | B7 | 25 Gly | G1 | 94 Asp | G1 | 99 Asp |
| B8 | 27 Glu | B8 | 26 Glu | G2 | 95 Pro | G2 | 100 Pro |
| B9 | 28 Ala | B9 | 27 Ala | G3 | 96 Val | G3 | 101 Glu |
| B10 | 29 Leu | B10 | 28 Leu | G4 | 97 Asn | G4 | 102 Asn |
| B11 | 30 Glu | B11 | 29 Gly | G5 | 98 Phe | G5 | 103 Phe |
| B12 | 31 Arg | B12 | 30 Arg | G6 | 99 Lys | G6 | 104 Arg |
| B13 | 32 Met | B13 | 31 Leu | G7 | 100 Leu | G7 | 105 Leu |
| B14 | 33 Phe | B14 | 32 Leu | G8 | 101 Leu | G8 | 106 Leu |
| B15 | 34 Leu | B15 | 33 Val | G9 | 102 Ser | G9 | 107 Gly |
| B16 | 35 Ser | B16 | 34 Val | G10 | 103 His | G10 | 108 Asn |
| C1 | 36 Phe | C1 | 35 Tyr | G11 | 104 Cys | G11 | 109 Val |
| C2 | 37 Pro | C2 | 36 Pro | G12 | 105 Leu | G12 | 110 Leu |
| C3 | 38 Thr | C3 | 37 Trp | G13 | 106 Leu | G13 | 111 Val |
| C4 | 39 Thr | C4 | 38 Thr | G14 | 107 Val | G14 | 112 Cys |
| C5 | 40 Lys | C5 | 39 Gln | G15 | 108 Thr | G15 | 113 Val |
| C6 | 41 Thr | C6 | 40 Arg | G16 | 109 Leu | G16 | 114 Leu |
| C7 | 42 Tyr | C7 | 41 Phe | G17 | 110 Ala | G17 | 115 Ala |
| CE1 | 43 Phe | CD1 | 42 Phe | G18 | 111 Ala | G18 | 116 His |
| CE2 | 44 Pro | CD2 | 43 Glu | G19 | 112 His | G19 | 117 His |

TABLE 2-continued

Amino Acid Sequence and Helical Residue Notation for Human Haemoglobin A$_O$

| Helix | α | Helix | β | Helix | A | Helix | β |
|---|---|---|---|---|---|---|---|
| CE3 | 45 His | CD3 | 44 Ser | GH1 | 113 Leu | GH1 | 118 Phe |
| CE4 | 46 Phe | CD4 | 45 Phe | GH2 | 114 Pro | GH2 | 119 Gly |
| — | — | CD5 | 46 Gly | GH3 | 115 Ala | GH3 | 120 Lys |
| CE5 | 47 Asp | CD6 | 47 Asp | GH4 | 116 Glu | GH4 | 121 Glu |
| CE6 | 48 Leu | CD7 | 48 Leu | GH5 | 117 Phe | GH5 | 122 Phe |
| CE7 | 49 Ser | CD8 | 49 Ser | H1 | 118 Thr | H1 | 123 Thr |
| CE8 | 50 His | D1 | 50 Thr | H2 | 119 Pro | H2 | 124 Pro |
| — | — | D2 | 51 Pro | H3 | 120 Ala | H3 | 125 Pro |
| — | — | D3 | 52 Asp | H4 | 121 Val | H4 | 126 Val |
| — | — | D4 | 53 Ala | H5 | 122 His | H5 | 127 Gln |
| — | — | D5 | 54 Val | H6 | 123 Ala | H6 | 128 Ala |
| — | — | D6 | 55 Met | H7 | 124 Ser | H7 | 129 Ala |
| CE9 | 51 Gly | D7 | 56 Gly | H8 | 125 Leu | H8 | 130 Tyr |
| E1 | 52 Ser | E1 | 57 Asn | H9 | 126 Asp | H9 | 131 Gln |
| E2 | 53 Ala | E2 | 58 Pro | H10 | 127 Lys | H10 | 132 Lys |
| E3 | 54 Gln | E3 | 59 Lys | H11 | 128 Phe | H11 | 133 Val |
| E4 | 55 Val | E4 | 60 Val | H12 | 129 Leu | H12 | 134 Val |
| E5 | 56 Lys | E5 | 61 Lys | H13 | 130 Ala | H13 | 135 Ala |
| E6 | 57 Gly | E6 | 62 Ala | H14 | 131 Ser | H14 | 136 Gly |
| E7 | 58 His | E7 | 63 His | H15 | 132 Val | H15 | 137 Val |
| E8 | 50 Gly | E8 | 64 Gly | H16 | 133 Ser | H16 | 138 Ser |
| E9 | 60 Lys | E9 | 65 Lys | H17 | 134 Thr | H17 | 139 Asn |
| E10 | 61 Lys | E10 | 66 Lys | H18 | 135 Val | H18 | 140 Ala |
| E11 | 62 Val | E11 | 67 Val | H19 | 136 Leu | H19 | 141 Leu |
| E12 | 63 Ala | E12 | 68 Leu | H20 | 137 Thr | H20 | 142 Ala |
| E13 | 64 Asp | E13 | 69 Gly | H21 | 138 Ser | H21 | 143 His |
| E14 | 65 Ala | E14 | 70 Ala | HC1 | 139 Lys | HC1 | 144 Lys |
| E15 | 66 Leu | E15 | 71 Phe | HC2 | 140 Tyr | HC2 | 145 Tyr |
| E16 | 67 Thr | E16 | 72 Ser | HC3 | 141 Arg | HC3 | 146 His |

In certain embodiments, wherein the modified protein is a haemoglobin beta chain subunit the at least one modification is βT84Y.

In certain embodiments, the at least one modification is βF85Y.

In certain embodiments, the at least one modification is βL96Y.

In certain embodiments, the at least one modification is a plurality of modifications selected from βL96Y, βF85Y and/or βT84Y or a combination thereof.

In certain embodiments, wherein the modified protein is a haemoglobin alpha chain subunit the at least one modification is αL91Y.

In certain embodiments, the at least one modification is αL29F.

In certain embodiments, the at least one modification is plurality of modifications selected from αL29F and/or αL91Y or a combination thereof.

In certain embodiments, wherein the modified protein is a haemoglobin gamma 1 chain subunit the at least one modification is γ1V67F.

In certain embodiments, the at least one modification is γ1L96Y.

In certain embodiments, the at least one modification is a plurality of modifications selected from γ1L96Y and/or γ1V67F or a combination thereof.

In certain embodiments, wherein the modified protein is a haemoglobin gamma 2 chain subunit the at least one modification is γ2V67F.

In certain embodiments, the at least one modification is γ2L96Y.

In certain embodiments, the at least one modification is a plurality of modifications selected from γ2L96Y and/or γ2V67F or a combination thereof.

The numbering used above for certain embodiments of the present invention wherein the modified protein is a haemoglobin chain subunit refers to the amino acid residue positions with reference to the wild-type human haemoglobin beta, alpha, gamma 1 and gamma 2 chain subunit amino acid sequences as set forth in SEQ ID NO: 1, SEQ ID NO: 2, SEQ ID NO: 3 and SEQ ID NO: 4 respectively. It will be understood by those skilled in the art that in certain embodiments wherein the modified protein comprises further modifications such as deletions or insertions the numbering of the above-mentioned modifications will change. By way of example if the N-terminus amino acid residue is deleted the modification βT84Y would change to be βT83Y and so on. If an amino acid residue is inserted at the N-terminus of the modified protein the modification βT84Y would be denoted as βT85Y. For example in certain embodiments the N-terminal of the protein may include a methionine residue encoded by the start codon which is usually cleaved from the mature protein, in such embodiments a T84Y modification would be denoted as T85Y, a F85Y modification would be denoted F86Y and a L91Y modification would be denoted L92Y and so on.

In one aspect of the present invention there is provided an amino acid sequence encoding for a modified oxygen-carrying protein, wherein said modification introduces or enhances reduction of at least one metallic ion and increases a rate at which an oxidised form of the modified oxygen-carrying protein is capable of re-oxygenation to an oxygen-binding form as compared to a reference protein.

In certain embodiments of the present invention there is provided a modified protein comprising an amino acid sequence having at least 80% sequence identity to the sequence as set forth in SEQ ID NO: 9.

In certain embodiments, the modified protein has at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 9.

In certain embodiments of the present invention there is provided a modified protein comprising an amino acid sequence having at least 80% sequence identity to the sequence as set forth in SEQ ID NO: 10.

In certain embodiments, the modified protein has at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 10.

In certain embodiments of the present invention there is provided a modified protein comprising an amino acid sequence having at least 80% sequence identity to the sequence as set forth in SEQ ID NO: 11.

In certain embodiments, the modified protein has at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 11.

In certain embodiments of the present invention there is provided a modified protein comprising an amino acid sequence having at least 80% sequence identity to the sequence as set forth in SEQ ID NO: 12.

In certain embodiments, the modified protein has at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 12.

In certain embodiments of the present invention there is provided a modified protein comprising an amino acid sequence having at least 80% sequence identity to the sequence as set forth in SEQ ID NO: 13.

In certain embodiments, the modified protein has at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 13.

In certain embodiments of the present invention there is provided a modified protein comprising an amino acid sequence having at least 80% sequence identity to the sequence as set forth in SEQ ID NO: 14.

In certain embodiments, the modified protein has at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 14.

In certain embodiments of the present invention there is provided a modified protein comprising an amino acid sequence having at least 80% sequence identity to the sequence as set forth in SEQ ID NO: 15.

In certain embodiments, the modified protein has at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 15.

In certain embodiments of the present invention there is provided a modified protein comprising an amino acid sequence having at least 80% sequence identity to the sequence as set forth in SEQ ID NO: 16.

In certain embodiments, the modified protein has at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 16.

In certain embodiments of the present invention there is provided a modified protein comprising an amino acid sequence having at least 80% sequence identity to the sequence as set forth in SEQ ID NO: 17.

In certain embodiments, the modified protein has at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 17.

In certain embodiments, the modified protein may be a myoglobin protein. An amino acid sequence of a human myoglobin amino acid sequence is shown in SEQ ID NO: 18. The human myoglobin sequence has accession number UniProt P02144. In certain embodiments, the modified protein is a human myoglobin protein having at least one modification to introduce a redox-active amino acid residue, whether by way of insertion or substitution.

In one aspect of the present invention there is provided a nucleic acid sequence encoding a modified protein of the present invention.

In certain embodiments, the nucleic acid sequence may be DNA or RNA. In certain embodiments, the sequence may be double stranded DNA. In certain embodiments, the sequence may be single stranded DNA.

In certain embodiments, the nucleic acid sequence is isolated and/or purified. In certain embodiments, the nucleic acid sequence is substantially free or free from material which it may be associated with.

In certain embodiments, the nucleic acid sequence of the present invention may be obtained by modification of a wild-type nucleic acid encoding an oxygen-carrying protein. The nucleic acid sequences encoding for oxygen-carrying proteins such as haemoglobin and haemoglobin chain sub-units will be known by those skilled in the art.

In certain embodiments, recombinant DNA techniques such as site directed mutagenesis may be used to modify a nucleic acid sequence such that the nucleic acid sequence encodes for a modified protein of the present invention. Other suitable methods will be known by those skilled in the art.

In certain embodiments, the nucleic acid sequence of the present invention may be incorporated into a recombinant replicable vector. In certain embodiments, the vector is used to replicate the nucleic acid in a compatible host cell.

Thus, in a further aspect of the present invention there is provided a method of producing a modified protein as described herein comprising the steps of introducing a nucleic acid encoding the modified protein into a replicable vector, introducing the vector into a compatible host cell and culturing the host cell under conditions to bring about the replication of the vector.

In a further aspect of the present invention there is provided a method of producing a modified protein of the present invention comprising the steps of:
  transfecting a host cell with a nucleic acid of the present invention;
  inducing the host cell to express the modified protein of the present invention; and
  isolating the modified protein of the present invention.

In certain embodiments, the method further comprises a step of purifying the isolated modified protein of the present invention.

In one aspect of the present invention there is provided a composition comprising,
  a modified oxygen-carrying protein, wherein the protein comprises at least one modification which introduces or enhances reduction of at least one metallic ion and increases a rate at which an oxidised form of the modified oxygen-carrying protein is capable of re-oxygenation to an oxygen-binding form as compared to a reference protein; and a pharmaceutically acceptable carrier or diluents.

In certain embodiments, the composition comprises a modified protein as described above.

For example, in certain embodiments, the modified protein is a haemoglobin. In certain embodiments, the modified protein is a haemoglobin chain subunit. In certain embodiments, the haemoglobin chain subunit is haemoglobin beta chain subunit. In certain embodiments, the haemoglobin beta chain subunit is human haemoglobin beta chain subunit.

In certain embodiments, the modified protein comprises at least one human haemoglobin beta chain subunit wherein the at least one modification is βT84Y. In certain embodiments, the at least one modification is βF85Y. In certain embodiments, the at least one modification is βL96Y.

In certain embodiments the at least one modification is a plurality of modifications selected from βL96Y, βF85Y and/or βT84Y or a combination thereof.

In certain embodiment, the modified protein comprises at least one human haemoglobin alpha chain subunit wherein the at least one modification is αL91Y. In certain embodiments, the at least one modification is αL29F.

In certain embodiments, the at least one modification is plurality of modifications selected from αL29F and/or αL91Y or a combination thereof.

In certain embodiment, the modified protein comprises at least one human haemoglobin gamma 1 chain subunit wherein the at least one modification is γ1V67F. In certain embodiments, the at least one modification is γ1L96Y.

In certain embodiments, the at least one modification is a plurality of modifications selected from γ1L96Y and/or γ1V67F or a combination thereof.

In certain embodiments, wherein the modified protein is a haemoglobin gamma 2 chain subunit the at least one modification is γ2V67F.

In certain embodiments, the at least one modification is γ2L96Y.

In certain embodiments, the at least one modification is a plurality of modifications selected from γ2L96Y and/or γ2V67F or a combination thereof.

In certain embodiments, the composition further comprises at least one reductant. In certain embodiments, the at least one reductant is for donating at least one electron so as to reduce the at least one metallic ion.

In certain embodiments, the at least one reductant is ascorbate. In certain embodiments, the at least one reductant is Nicotinamide adenine dinucleotide phosphate (NADPH). In certain embodiments, the at least one reductant is Nicotinamide Adenine Dinucleotide (NADH). In certain embodiments, the reductant is one or more of ascorbate, NADP and/or NADH. Other suitable reductants will be known to those skilled in the art.

In certain embodiments, the composition is a pharmaceutical composition and is for administration to a subject. In certain embodiments, the subject is a mammalian subject. In certain embodiments, the subject is a human.

In certain embodiments, the composition is a blood substitute composition. A blood substitute composition is a composition which may be used to mimic and/or fulfil the functions of blood. Blood substitute compositions may include such components as plasma, serum albumin and other fluids of which are not derived from blood such as plasma volume expanders; these, may include for example crystalloid intravenous solutions. Other suitable blood substitute components will be known to those skilled in the art. The components of a blood substitute that is able to mimic bloods ability to carry and transfer oxygen may be referred to as an oxygen therapeutic. Thus, in certain embodiments the modified protein and compositions thereof, of the present invention may be referred to as oxygen therapeutics.

In certain embodiments, the composition is a resuscitation fluid. Resuscitation fluids are fluids that may be used to restore intravascular volume. Without being bound by theory resuscitation fluids may be broadly categorized into two main categories, colloid and crystalloid solutions. Colloid solutions are suspensions of molecules within a carrier solution that are relatively incapable of crossing a healthy semipermeable capillary membrane owing to the molecular weight of the molecules. Crystalloids are solutions of ions that are freely permeable but contain concentrations of salts such as sodium and/or chloride that determine the tonicity of the fluid. By way of example resuscitation fluids may include at least one or more of sodium, potassium, calcium, magnesium, chloride, acetate, lactate, malate, gluconate, bicarbonate or octanoate. Other suitable resuscitation fluid components will be known by those skilled in the art.

In one aspect of the present invention there is provided a modified protein and compositions thereof of embodiments of the present invention for use as a medicament.

In certain embodiments, the modified protein is a haemoglobin. In certain embodiments, the modified protein is a haemoglobin chain subunit. In certain embodiments, the haemoglobin chain subunit is haemoglobin beta chain subunit. In certain embodiments, the haemoglobin beta chain subunit is human haemoglobin beta chain subunit.

In certain embodiments, the modified protein comprises at least one human haemoglobin beta chain subunit wherein the at least one modification is βT84Y. In certain embodiments, the at least one modification is βF85Y. In certain embodiments, the at least one modification is βL96Y.

In certain embodiments, the at least one modification is a plurality of modifications selected from βL96Y, βF85Y and/or βT84Y or a combination thereof.

In certain embodiment, the modified protein comprises at least one human haemoglobin alpha chain subunit wherein the at least one modification is αL91Y. In certain embodiments, the at least one modification is αL29F.

In certain embodiments, the at least one modification is plurality of modifications selected from αL29F and/or αL91Y or a combination thereof.

In certain embodiments, the modified protein comprises at least one human haemoglobin gamma 1 chain subunit wherein the at least one modification is γ1V67F. In certain embodiments, the at least one modification is γ1L96Y.

In certain embodiments, the at least one modification is a plurality of modifications selected from γ1L96Y and/or γ1V67F or a combination thereof.

In certain embodiments, wherein the modified protein is a haemoglobin gamma 2 chain subunit the at least one modification is γ2V67F.

In certain embodiments, the at least one modification is γ2L96Y.

In certain embodiments, the at least one modification is a plurality of modifications selected from γ2L96Y and/or γ2V67F or a combination thereof.

Further details of the modified protein are provided herein.

The modified proteins and compositions thereof of embodiments the present invention may be for use as an oxygen therapeutic. As used herein the term "oxygen therapeutic" refers to a molecule that is able to transport and release oxygen. Oxygen therapeutics may be used as part of a blood substitute or may be referred to as a blood substitute themselves by those of ordinary skill in the art.

Modified proteins and compositions thereof of embodiments the present invention may be for use in conditions wherein there is a need for the restoration, maintenance or replacement of oxygen. These include but are not limited to one or more of trauma; ischemia (such as ischemia induced by heart attack, stroke or cerebrovascular trauma); hemodilution (where an oxygen therapeutic is required to replace blood that is removed pre-operatively); septic shock; cancer; chronic anaemia; sickle cell anaemia; cardioplegia; hypoxia; haemorrhaging (blood loss due to trauma and/or surgical procedures) and/or carbon monoxide poisoning. Thus in certain embodiments the modified proteins and compositions thereof as described herein may be for use in the treatment of the above-mentioned conditions. Other suitable uses will be known by those skilled in the art.

In certain embodiments, the modified proteins and compositions thereof as described herein are for use in the treatment of ischemia.

In certain embodiments, the modified proteins and compositions thereof as described herein are for use in the treatment and/or prevention of hypoxia.

In certain embodiments, the modified proteins and compositions thereof as described herein are for use in the treatment and/or prevention of ischemia and/or hypoxia.

Ischemia is a lack of and/or reduced blood flow to an organ or tissue. Ischemia may be caused by a blockage within one or more blood vessels or due to external compression of one or more blood vessels. By way of example a blockage within a blood vessel may be a thrombus or atherosclerosis. Such blockages may be arterial blockages or venous blockages, other blockages will be known by those skilled in the art and may cause what is known in the art as arterial or venous insufficiency. By way of example external compression of a blood vessel may be caused by trauma which may induce swelling and/or inflammation therefore constricting the blood vessels or may be caused by an external object and/or internal tissue such as a tumour or cancerous growth or inflamed organ applying pressure to a blood vessel. Ischemia may also occur when blood loss occurs such as due to acute haemorrhage, due to trauma or during surgical procedures. Types of ischemia will be known by those skilled in the art but non-limiting examples include myocardial ischemia, cerebral ischemia, limb ischemia, mesenteric ischemia and/or cutaneous ischemia.

As red blood cells normally carry 98% of the oxygen in blood to cells, tissues and organs, ischemia may lead to hypoxia. Hypoxia is a lack of and/or reduced amount of oxygen being transported to cells, tissues or organs and may be defined as a decrease in the oxygen tension within a tissue below normal functioning levels. Oxygen tension is a measure of the partial pressure of oxygen within blood and/or a tissue. Oxygen transfer from blood vessels, such as a capillary to associated tissue or cells may be characterised in terms of oxygen flux. As used herein the term "oxygen flux" refers to the mass of oxygen transported through a blood vessel per unit of time. When blood flow is reduced as may be caused for example by blood loss (haemorrhage), ischemia and/or shock (e.g. volume deficiency shock, anaphylactic shock, septic shock or allergic shock) a reduced amount of red blood cells flow through the blood vessel and therefore the oxygen flux decreases, therefore leading to a decrease in the transfer of oxygen to associated cells or tissue thereby resulting in hypoxia and in some cases anoxia, which is characterised as a tissue condition wherein no measurable oxygen is present. Both hypoxia and anoxia may lead to death of cells and/or tissue (necrosis). Thus certain embodiments of the modified proteins and compositions thereof, of the present invention may be for use in the treatment and/or prevention of hypoxia and/or anoxia and therefore may be for use in the prevention of necrosis.

Thus in one aspect of the present invention there is provided a method of treating and/or preventing ischemia comprising administering to a subject in need thereof a pharmaceutically effective amount of a pharmaceutical composition comprising a modified oxygen-carrying protein comprising at least one modification, wherein said modification introduces or enhances reduction of at least one metallic ion and increases a rate at which an oxidised form of the modified oxygen-carrying protein is capable of re-oxygenation to an oxygen-binding form as compared to a reference protein.

In certain embodiments, the method is for the treatment and/or prevention of hypoxia.

In certain embodiments, the method is for the treatment and/or prevention of ischemia and/or hypoxia.

In certain embodiments, the method comprises the use of a modified protein as described herein. In certain embodiments, the modified protein is haemoglobin. In certain embodiments, the modified protein is a haemoglobin chain subunit. In certain embodiments, the haemoglobin chain subunit is haemoglobin beta chain subunit. In certain embodiments, the haemoglobin beta chain subunit is human haemoglobin beta chain subunit.

In certain embodiments, the modified protein comprises at least one human haemoglobin beta chain subunit wherein the at least one modification is βT84Y. In certain embodiments, the at least one modification is βF85Y. In certain embodiments, the at least one modification is βL96Y.

In certain embodiments, the at least one modification is a plurality of modifications selected from one or more of βL96Y, βF85Y and βT84Y or a combination thereof.

In certain embodiment, the modified protein comprises at least one human haemoglobin alpha chain subunit wherein the at least one modification is αL91Y. In certain embodiments, the at least one modification is αL29F.

In certain embodiments, the at least one modification is plurality of modifications selected from one or more of αL29F and αL91Y or a combination thereof.

In certain embodiment, the modified protein comprises at least one human haemoglobin gamma 1 chain subunit wherein the at least one modification is γ1V67F. In certain embodiments, the at least one modification is γ1L96Y.

In certain embodiments, the at least one modification is a plurality of modifications selected from one or more of γ1L96Y and γ1V67F or a combination thereof.

In certain embodiments, wherein the modified protein is a haemoglobin gamma 2 chain subunit the at least one modification is γ2V67F.

In certain embodiments, the at least one modification is γ2L96Y.

In certain embodiments, the at least one modification is a plurality of modifications selected from one or more of γ2L96Y and γ2V67F or a combination thereof.

In a further aspect of the present invention there is provided a method of treating and/or preventing ischemia, the method comprising administering a pharmaceutically effective amount of a modified oxygen-carrying protein comprising at least one modification, wherein said modification introduces or enhances reduction of at least one metallic ion and increases a rate at which an oxidised form of the modified oxygen-carrying protein is capable of re-oxygenation to an oxygen-binding form as compared to a reference protein.

In certain embodiments, the method is for the treatment and/or prevention of hypoxia.

In certain embodiments, the method is for the treatment and/or prevention of ischemia and/or hypoxia.

In certain embodiments, the modified protein is haemoglobin. In certain embodiments, the modified protein is a haemoglobin chain subunit. In certain embodiments, the haemoglobin chain subunit is haemoglobin beta chain subunit. In certain embodiments, the haemoglobin beta chain subunit is human haemoglobin beta chain subunit.

Details of the Modified Protein are Provided Herein

As used herein an "effective" amount or a "therapeutically effective amount" of a protein refers to a nontoxic but sufficient amount of the protein to provide the desired effect. The amount that is "effective" will vary from subject to subject, depending on the age and general condition of the individual, mode of administration, and the like. An appropriate "effective" amount in any individual case may be determined by one of ordinary skill in the art using routine experimentation.

Certain embodiments of the modified proteins and compositions described herein may be for use as a bridge to red blood cell transfusion. The term "bridge to red blood cell transfusion" as used herein refers to when red blood cell transfusion is a viable treatment but is delayed. Therefore the use of certain embodiments of the modified protein and compositions thereof described herein may help to prevent and/or treat ischemia and/or hypoxia that may occur, until a red blood cell transfusion can be performed. By way of example certain embodiments of the modified proteins and compositions thereof may be used in situations when no red blood cells are readily available, such as on a battlefield or in remote areas and/or when suitable red blood cells cannot be readily matched to the blood type of a subject in need thereof or when amounts of red blood cells are not sufficient for treatment such as when treating large numbers of subjects in need thereof.

Certain embodiments of the modified proteins and compositions described herein may be for use as an alternative to red blood cell transfusion. By way of example certain embodiments of the modified proteins and compositions described herein may be used when a subject in need thereof rejects a red blood cell transfusion, such as for religious regions and/or when repetitive red blood cell transfusions over a substantial time period are required, such as subject suffering from anaemia or anaemia related disease and/or where no suitable red blood cells are available such as in developing countries.

Certain embodiments of the modified proteins and compositions described herein may be for use in the protection and/or maintenance of the functioning of organs at risk due to medical conditions and/or surgical procedures e.g. the brain, spinal cord, heart, kidney or gut.

Certain embodiments of the modified proteins and compositions as described herein may be for use in the maintenance of ex vivo organs and/or tissues. By way of example transplant organs wherein oxygen content is needed to be maintained to ensure the organ is in an acceptable condition to be transplanted into a subject in need thereof. By way of example organs may include at least one of heart, liver, lung or kidney.

The terms "patient", "subject" and "individual" may be used interchangeably and refer to either a humans or non-human mammal. In certain embodiments, the subject is a human.

The therapeutically effective amount of the modified proteins and compositions as described herein will depend on the route of administration, the type of subject being treated, and the physical characteristics of the specific subject under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. Certain embodiments of the modified proteins and compositions thereof of the present disclosure may be particularly useful for treatment of humans.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the person skilled in the art.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, arginine, lysine, or acetate or mixtures thereof. The term further encompasses any agents listed in the US Pharmacopeia for use in animals, including humans.

"Treatment" is an approach for obtaining beneficial or desired clinical results. For the purposes of the present disclosure, beneficial or desired clinical results include, but are not limited to, alleviation of symptoms, diminishment of extent of disease, stabilized (i.e. not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms when compared to the absence of treatment, and is not necessarily meant to imply complete cessation of the relevant condition.

Certain embodiments of the modified proteins and compositions described herein may be for use in cell, tissue, or organ culturing and/or preservation. In certain embodiments, the modified proteins and compositions thereof may be used alone or in addition to one or more further oxygen carrying proteins and/or in addition to a culture and/or preservation media suitable for cell culture, tissue culture and/or organ culture and/or tissue and/or organ perfusion. Without being bound by theory, certain embodiments of the modified proteins as described herein may help to increase the oxygen transported to said cells, tissues and/or organs and therefore increase the probability of maintaining healthy normal living cells, tissue or organs.

In certain embodiments, the modified proteins and compositions described herein may also extend the lifetime of cultured cells, tissues or organs. Thus, in certain embodiments, there is provided a composition which comprises a modified protein described herein and a cell culture media. In certain embodiments, the cell culture media is a liquid medium and may be selected from Viaspan®, 1 IGL®, Celsior®, SCOT Maco®, BMPS Belzer®, Custodiol® (HTK), Euro-Collins®, Soltran®, Perfadex®, Ringer lactate® and/or Plegisol®, Dulbecco's Modified Eagle Medium/Nutrient Mixture F-12, minimal essential media, Roswell Park Memorial Institute medium 1640 or 199 and/or any medium composition suitable for preservation of organs, tissues, or organ cells or tissue, or suitable for organ or tissue perfusion.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

Materials and Methods

Production of Recombinant Haemoglobin and Modified Proteins

The methods used were as performed as in "Reeder et al. Tyrosine Residues as Redox Cofactors in Human Haemoglobin: Implications For Engineering Nontoxic Blood Substitutes. *J Biol Chem.* 2008 Nov. 7; 283(45):30780-7" which is incorporated herein by reference. A summary of the methods used is given below.

Genes from human haemoglobin (Hb) α and β chain subunits were optimised for expression in *Escherichia Coli* (*E coli*) and cloned into the vector pETDuet to form HbpETDuet. Mutagenesis was performed by Epoch Life Sciences (Sugar land, Texas). Modified and unmodified plasmids were transformed into *E coli* BL21 DE3 cells using standard procedures. Resulting mutant clones were sequenced with BigDye terminator version 3.1 (Applied Biosystems Inc, Foster City, CA) to confirm correct sequences. *E. coli* BL21 DE3 cells harbouring the plasmid HbpETDuet encoding for a reference or modified Hb was grown in 2-liter Erlenmeyer flasks containing 1 litre of Terrific Broth medium with 100 μg/ml carbenicillin at 37° C. and 120 rpm until $A_{620}$ 21. Expression of reference Hb or modified Hb was then induced by adding 0.1 mM isopropyl 1-thio-β-D-galactopyranoside, 0.3 mM δ-aminolevulinic acid, and CO gas. Culture conditions after induction were 22° C. and 60 rpm. Cells were harvested and suspended in 10 mM sodium phosphate buffer, pH 6.0, before sonication. Following centrifugation for 1 hour at 20,000 rpm, the supernatant was adjusted to pH 6.2 and filtrated using a 0.45-μm Minisart filter (Sartorius). The reference Hb or modified Hb was purified using ion exchange chromatography with CM-Sepharose FF column (GE Healthcare). After sample application, the column was washed with 10 mM sodium phosphate buffer, pH 6.0, until absorbance of eluted fractions returned to a base line absorbance value. The reference Hb or modified Hb was eluted with 70 mM sodium phosphate buffer, pH 7.2, and concentrated using Viva-Spin columns (Vivascience, 30-kDa molecular mass cutoff). The concentrated sample was then applied to a Sephacryl S-200 gel filtration column (GE Healthcare) using elution buffer on an AKTA purifier system. Globin-containing fractions were concentrated as above, flash-frozen in liquid nitrogen, and stored at −80° C.

Prior to ferryl reduction experimentation, the reference Hb or modified Hb was oxidized to the ferric form by the addition of a 1.5 M excess potassium ferricyanide following CO removal by shining light on the sample with gentle oxygenation using a stream of oxygen gas. Ferri-ferrocyanide was removed by filtration through a Sephadex G-25 column (10×1 cm). Concentration of reference Hb or modified Hb was determined from reduction of an aliquot of the ferric Hb using sodium dithionite to the deoxy form.

Autoxidation Measurements

The rate of conversion of ferrous oxy-haemoglobin to ferric met-haemoglobin was monitored by UV-visible spectroscopy. A 1 ml solution of 20 mM sodium phosphate (pH 7.4) with a protein concentration of 10 μM haem were studied at either 25° C. or 37° C. For samples at 25° C. spectra between 375-700 nm were collected for up to 48 hours. For samples at 37° C. spectra between 375-700 nm were collected for up to 3 hours. Kinetic traces were analysed by fitting to single exponential fits.

Haem Release from Haemoglobin

Recombinant HbA (final concentration of 1.7 μM) was mixed with an excess of the haem binding protein hemopexin (final concentration 2 μM) at 37° C. in sodium phosphate buffer (20 mM, pH 7.2). The rate of change of haem from high spin in met-haemoglobin to low spin when bound by hemopexin was monitored by measuring optical changes in the Soret and visible regions of the optical spectra. The rate of release was monitored by measuring the increase in the difference between absorbance at 425 nm and 495 nm. Or the decrease in the difference between absorbance at 401 nm and 495 nm. Time courses were analysed by single exponential fits. Absorbance measurements were taken using an Agilent Cary 5000 spectrophotometer.

Ferryl Reduction Measurements

Samples of ferryl haemoglobin were made by adding $H_2O_2$ and ferric met-haemoglobin in a 3:1 ratio and incubating for 10-15 minutes. Full conversion was confirmed by analysing optical spectra from the Soret and visible regions. A small concentration of catalase (1-5 nM) (Sigma-Aldrich) was added to remove any excess $H_2O_2$ (Sigma Aldrich).

Seconds after addition of catalase, sodium ascorbate of varying concentrations was added to the sample and the reduction of ferryl haemoglobin to ferric met-haemoglobin was measured optically using the difference between absorbance measured at 535 nm and 630 nm (i.e. $Abs_{545}$ minus $Abs_{630}$). The time courses were fitted to double exponential fits assuming that full reduction was achieved half via α-chains and half via β-chains and forcing fits accordingly (i.e. an equal amplitude of absorbance for each of the chain types). The ascorbate concentration dependence of the pseudo-first order rate constants for α-chain and β-chain ferryl reduction were fitted to a double rectangular hyperbola, representing different electron transfer pathways. Buffer was 20 mM sodium phosphate pH 7.2, and experiments were performed at a temperature of 25° C., concentration of haemoglobin used was 10 µM. Absorbance measurements were taken using an Agilent Cary 5000 spectrophotometer.

Ferric Reduction Measurements

Ferric Haemoglobin at a concentration of 20 µM in sodium phosphate buffer (20 mM, pH 7.2) was mixed with sodium ascorbate in a 1:1 volume to volume ratio (to give a final concentration of ferric haemoglobin of 10 µM) at 25° C. The final concentration of sodium ascorbate was 0.1 mM, 1 mM or 10 mM. The reaction mix was monitored optically using a Cary 5000 spectrophotometer (Agilent) for a period of 1 to 4 hours. The time courses of absorbance at 577-630 nm were fitted to a single exponential function minimising the least squares using Microsoft Excel Solver.

The percentage of oxy-haemoglobin formed was calculated by normalising change in absorbance against the expected change in absorbance for total conversion of met-haemoglobin to oxy-haemoglobin.

Results

Autoxidation

The rate of autoxidation of ferrous oxy-haemoglobin can be seen for wild-type (wt) recombinant HbA protein, a βT84Y modified recombinant HbA protein, reference (V1M modified wild-type protein) recombinant HbA protein and a βT84Y (V1M) modified recombinant HbA protein in FIG. 1. Introducing a βT84Y modification can be seen to not result in increased autoxidation as compared to wild-type and V1M modified reference proteins. This indicates that the βT84Y modification results in a relatively stable modified protein that does not readily autoxidise. This further indicates therefore that a the βT84Y modified proteins may be less likely to autoxidise when in use.

Haem Release from Haemoglobin

Figure 2:
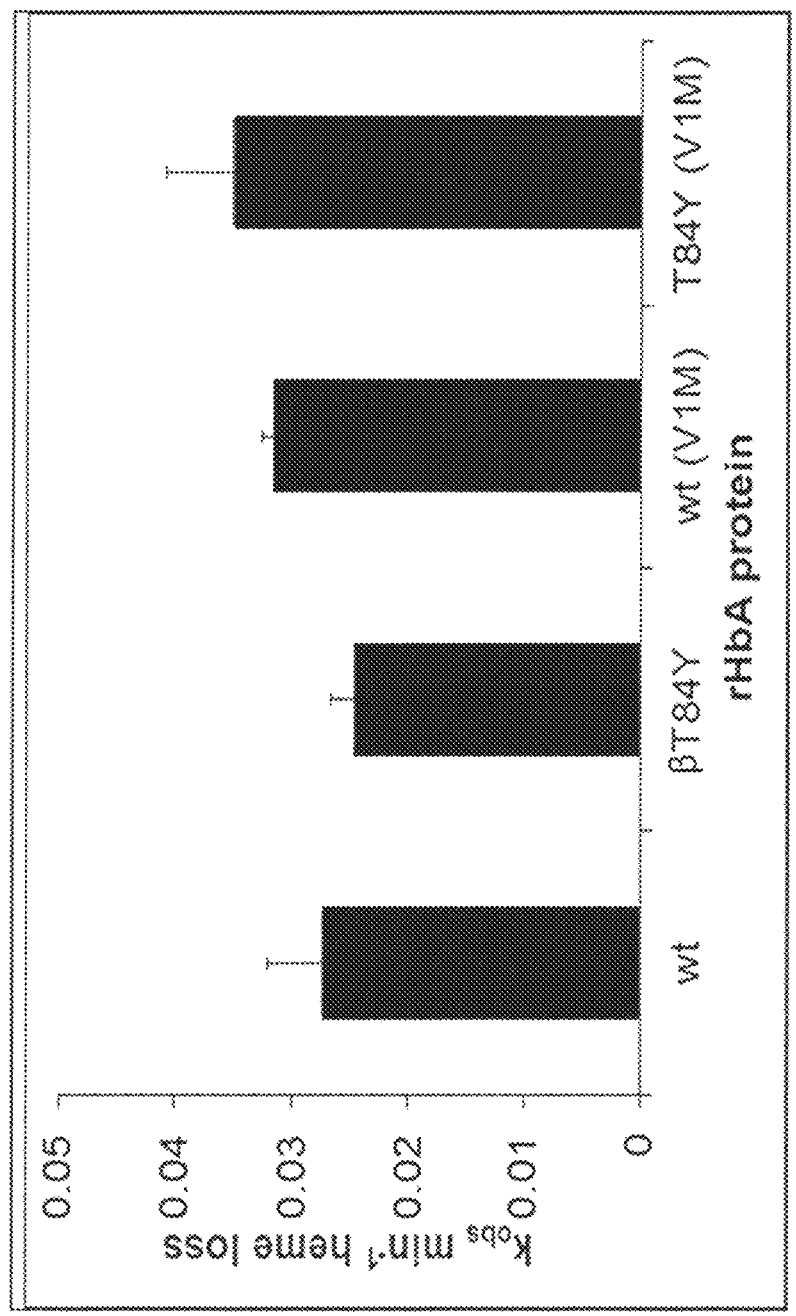
FIG. 2 illustrates the rate of haem loss from 1.7 μM recombinant HbA ferric met-haemoglobin for various reference proteins (wild-type HbA (wt) and V1M modified wild-type HbA (wt V1M)) and βT84Y modified protein and βT84Y (V1M) modified protein, to 2 μM hemopexin at 37° C. in sodium phosphate buffer (20 mM, pH 7.2). The bars are an average of 3 repeat experiments, standard deviations are shown by the error bars.

The rate of haem release from the met forms of wild-type (wt) recombinant HbA protein, a βT84Y modified recombinant HbA protein, a reference (V1M modified wild-type (wt(V1M)) recombinant HbA protein and a βT84Y (V1M) modified recombinant HbA protein can be observed in FIG. 2. No significant difference in the rate of haem loss can be observed for both βT84Y modified proteins as compared to wildtype and reference V1M modified proteins. This indicates that the βT84Y modification does not reduce binding of the haem group and so indicates that βT84Y modified proteins will retain binding of its haem cofactor when in use.

Ferryl Reduction

Figure 3:
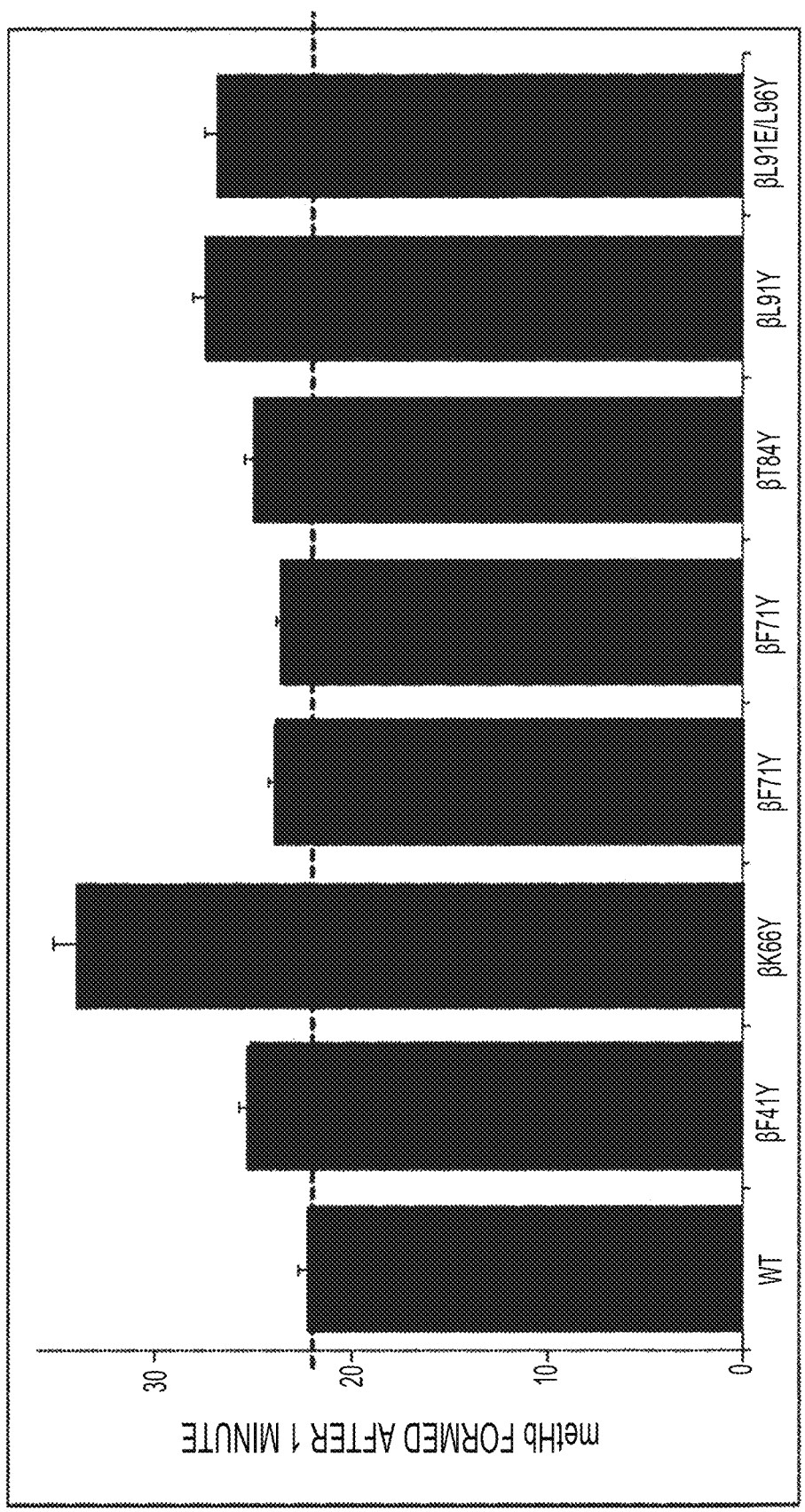
FIG. 3 illustrates the percentage of ferric met-haemoglobin formed from ferryl haemoglobin (10 μM) after incubation with ascorbate (30 μM) at 25° C. in sodium phosphate buffer (20 mM, pH 7.2) by various modified recombinant HbA proteins including beta chain subunit modifications and wild-type recombinant HbA. Each bar represents an average of 3 repeat experiments, standard deviations are shown by the error bars.

The percentage of ferryl haemoglobin reduced to ferric met-haemoglobin after 1 minute incubation with 30 µM ascorbate increases above that of the wild-type protein for all modified proteins studied (FIG. 3). This observation indicates that all the modified proteins studied are able to be reduced to the less toxic form of ferric met-haemoglobin under physiological conditions.

Ferric Reduction

Figure 4:
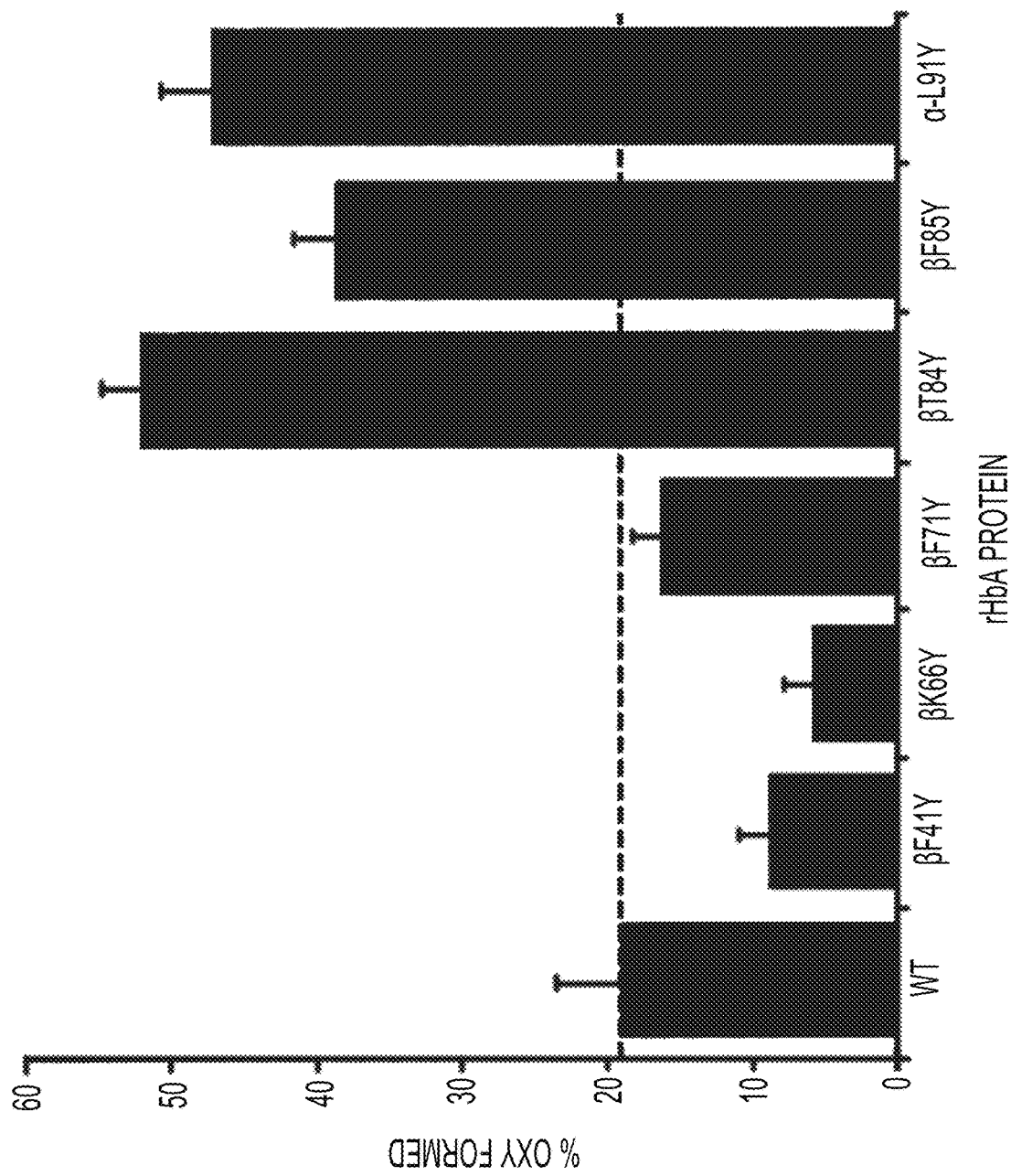
FIG. 4 illustrates the percentage, by various modified recombinant HbA proteins including at least one or more beta or alpha chain subunit modifications and wild-type recombinant HbA protein, of ferrous oxy-haemoglobin formed from ferric met-haemoglobin (10 μM) in the presence of ascorbate (100 μM) at 25° C. in sodium phosphate buffer (20 mM, pH 7.2).

The percentage of ferrous oxy-haemoglobin formed in the presence of 100 µM ascorbate over a time period of 60 minutes is observed to be increased for the βT84Y, βF85Y and αL91Y modified rHbA proteins in comparison to a wild-type protein as well as a number of other modified proteins that display ferryl haemoglobin to ferric met-haemoglobin reduction (FIG. 4).

Figure 5:
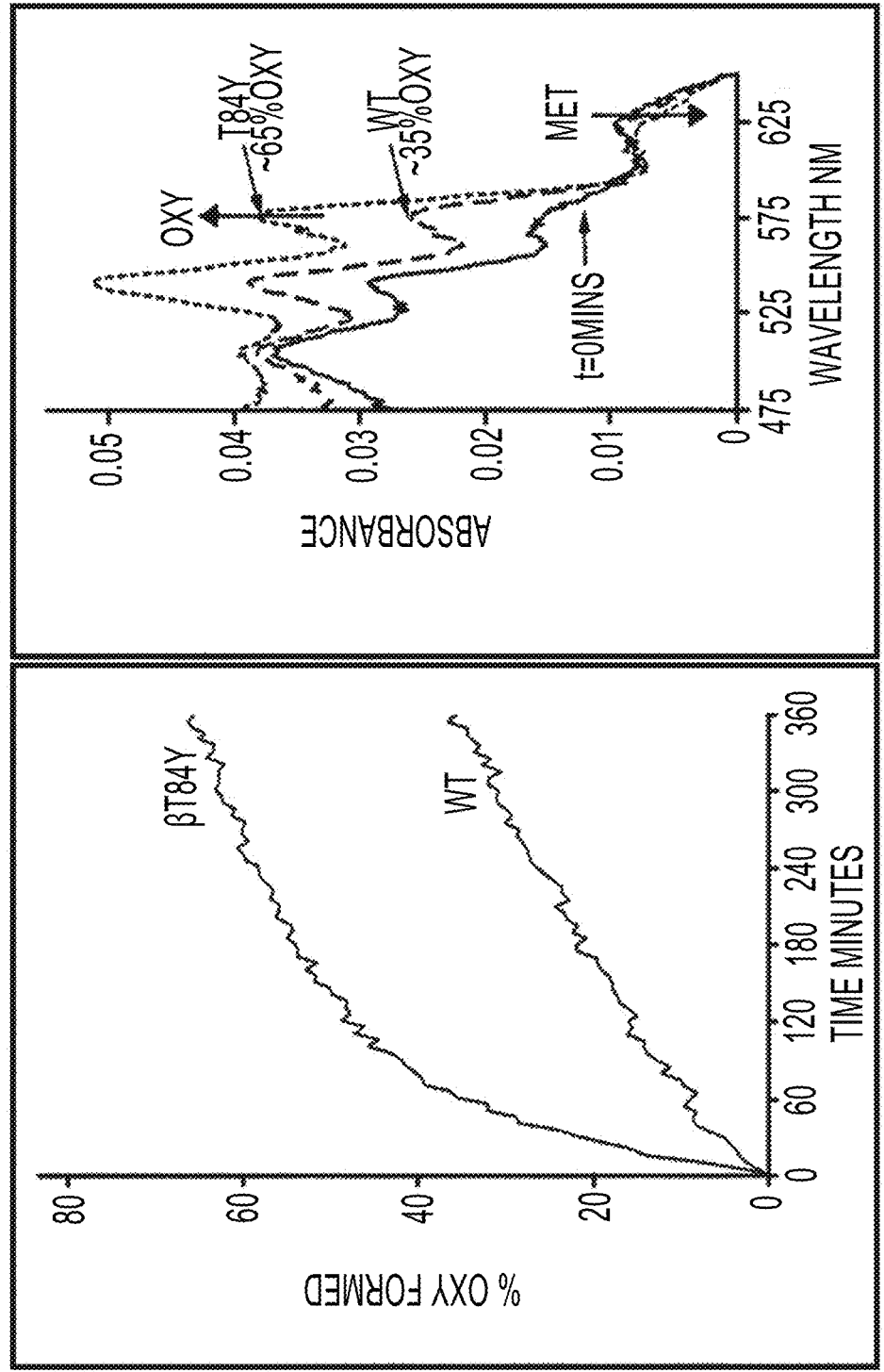
FIG. 5 illustrates a comparison of the capability of 4.4 μM of wild-type (wt) (long dashed line) and 4.4 μM βT84Y modified (short dashed line) recombinant HbA proteins to reduce ferric met-haemoglobin to ferrous oxy-haemoglobin over a time period of 360 minutes in the presence of ascorbate (100 μM) at 25° C. in sodium phosphate buffer (20 mM, pH 7.2). The black solid line shows the initial ferric met-haemoglobin spectrum.

The ability of the βT84Y modified protein to reduce ferric met-haemoglobin to ferrous oxy-haemoglobin is further shown by FIG. 5. It can be seen that in comparison to a wild-type protein that the rate of ferric oxy-haemoglobin production is greater than that of the wild-type protein (right hand graph) as is shown by the increased absorbance observed in the region for ferric oxy-haemoglobin for the βT84Y modified protein.

Figure 6:
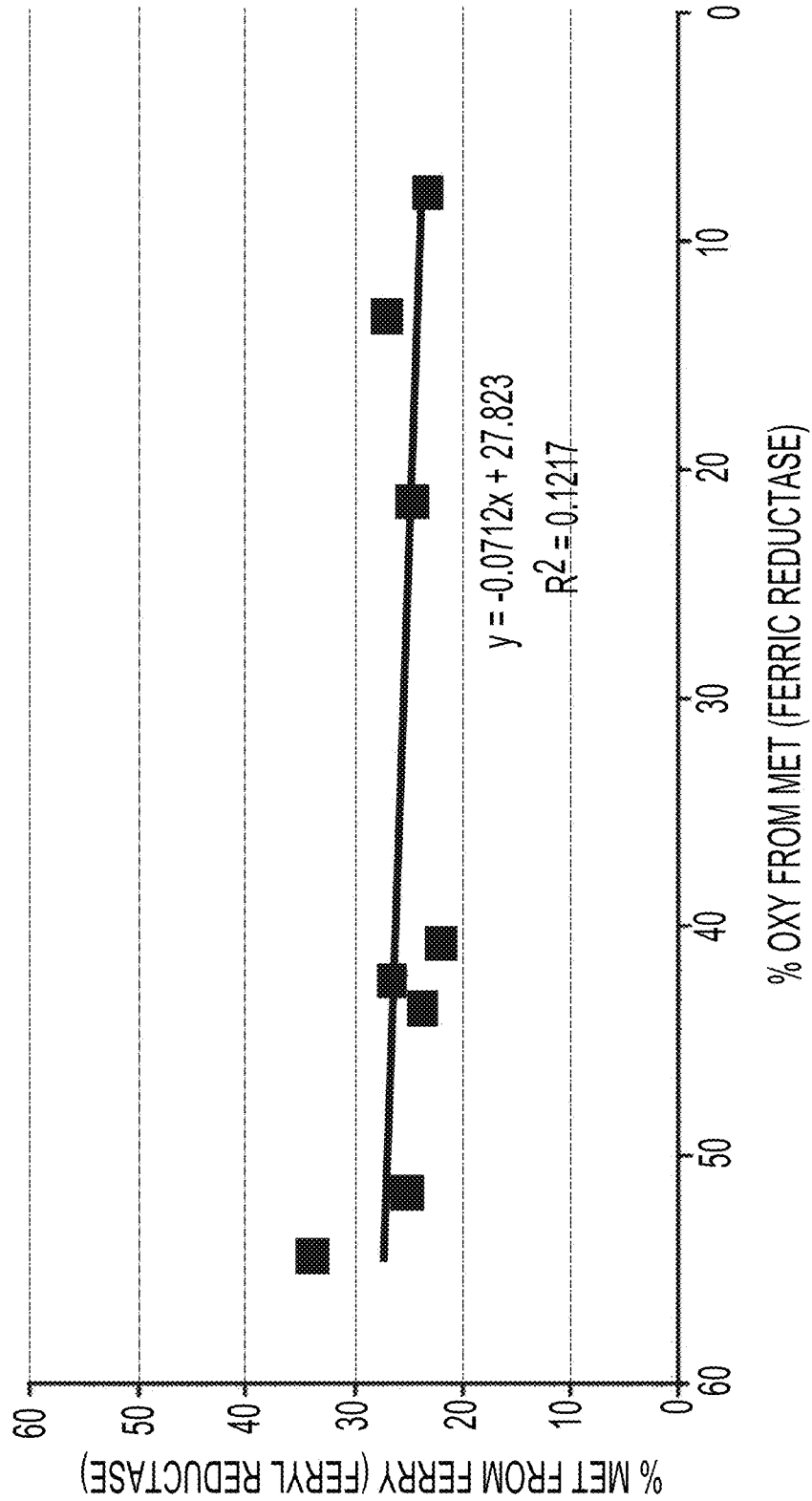
FIG. 6 illustrates the lack of a correlation between ferryl haemoglobin reduction ability and ferric met-haemoglobin reduction ability for various modified recombinant HbA proteins.

When the percentage of reduction of ferryl haemoglobin reduction to ferric met-haemoglobin reduction is plotted against the percentage of ferric met-haemoglobin to ferrous oxy-haemoglobin there is no correlation seen as is shown by FIG. 6.

Figure 12:
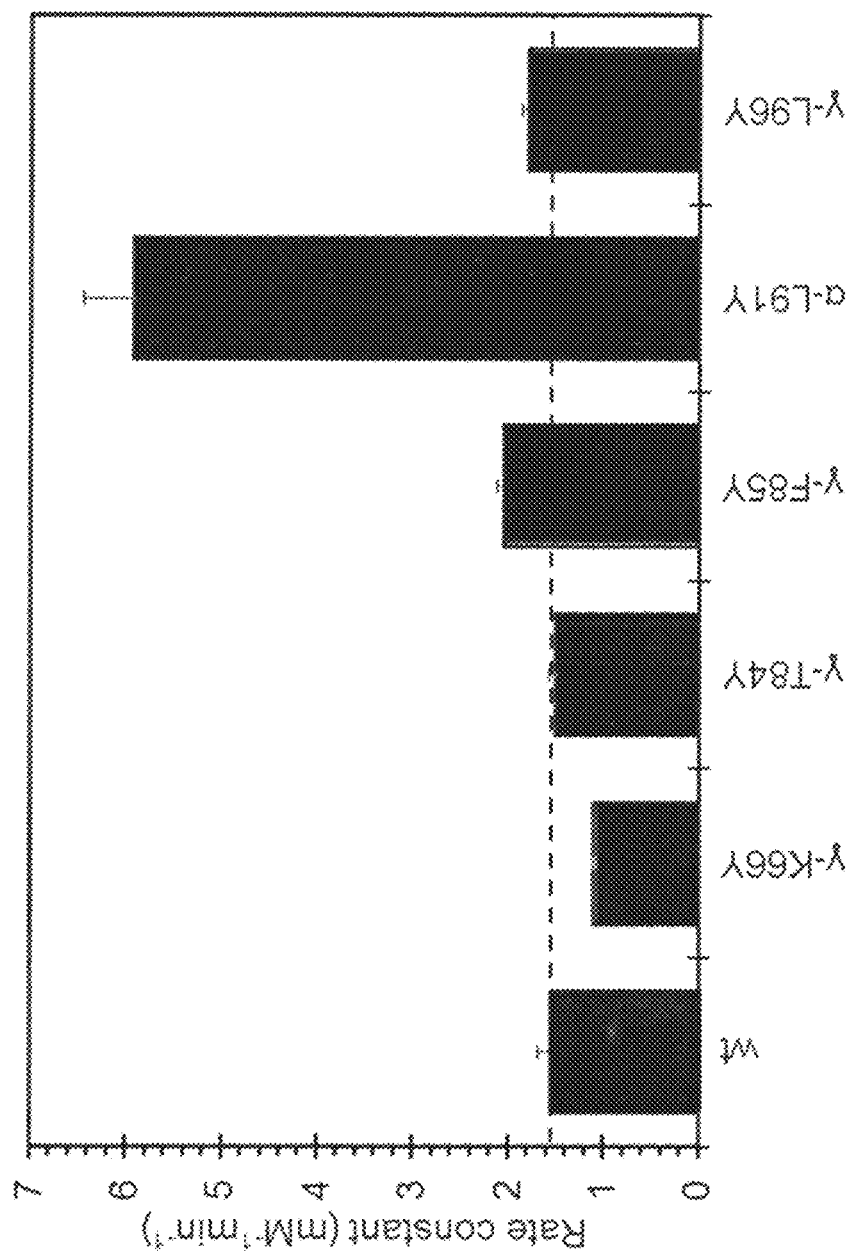
FIG. 12 illustrates a comparison of the rate of formation of ferrous (oxy-haemoglobin) formation from ferric (met-haemoglobin) for various modified recombinant foetal haemoglobins (HbF) in comparison to reference protein (wild type, WT). The time course (577-630 nm) was fitted to a single exponential function. The rate constants were plotted against ascorbate concentration and this was fitted to a straight line to determine the second order rate constant. Buffer used was sodium phosphate (70 mM, pH 7.2) and experiments were carried out at a temperature of 25° C. with haem present at 10 μM. Significantly increased rates of reduction (ferric-met to ferrous) were seen compared to wild-type for the mutations αL91Y, γF85Y and γL96Y.

Mutations in foetal haemoglobin are also able to enhance the reduction of ferric met-haemoglobin to ferrous oxy-haemoglobin. For example, the mutations αL91Y, γF85Y and γL96y show a significantly increased rate constant for ferric haem reduction by the external reductant ascorbate (FIG. 12).

Figure 7:
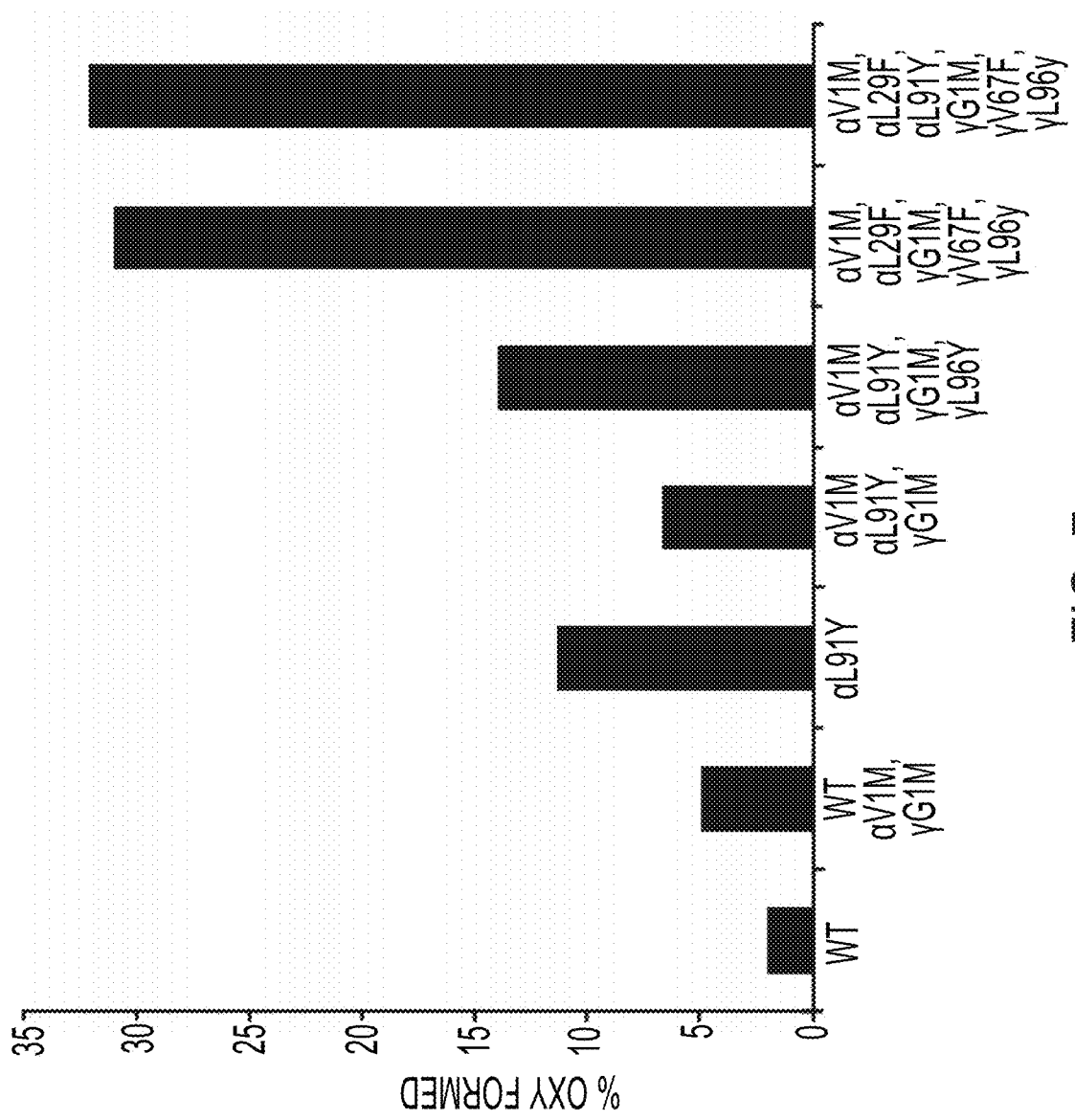
FIG. 7 illustrates a comparison of the percentage of ferrous (oxy-haemoglobin) formation from ferric (met-haemoglobin) for various modified recombinant foetal haemoglobins (HbF) in comparison to reference proteins (wild type (WT) and αV1M, γG1M modified HbF). Time scale of measurements was 60 minutes. Buffer used was sodium phosphate (20 mM, pH 7.2) and experiments were carried out at a temperature of 25° C. with haem present at 10 μM; and ascorbate present at 100 μM.

These modifications also function to enhance ferric haem reduction in the presence of additional mutations designed to improve protein production (G1M and/or V1M) or decrease NO scavenging (αL29F, γV67F). It can be seen from FIG. 7 that for modified proteins containing one or more haemoglobin chain subunits comprising one or more of the modifications αL29F, αL91Y, γV67F and γL96y with and without a further modification (G1 M and/or V1M) all show improved percentage of oxy-haemoglobin formed from met-haemoglobin in comparison to both wild-type and/or reference proteins. This indicates that the modifications singularly or in combination enhance or introduce reduction of haem group metal ions leading to formation of oxy-haemoglobin.

The invention claimed is:

1. A human hemoglobin protein comprising at least one modified human hemoglobin beta or gamma chain subunit, wherein:
   the beta chain subunit comprises SEQ ID NO:9 or 10 or the gamma chain subunit comprises SEQ ID NO:13 or 17.

2. The protein as claimed in claim 1, wherein the modified human hemoglobin further comprises at least one modified alpha chain subunit comprising SEQ ID NO:11, 12, 14 or 16.

3. The protein as claimed in claim 1, wherein:
   the protein is conjugated to at least one protecting group, optionally wherein the at least one protecting group is at least one antioxidant enzyme or polyalkylene glycol.

4. A multimeric protein, comprising the modified human hemoglobin beta or gamma chain subunit in claim 1; and
   two modified human hemoglobin alpha chain subunits comprising SEQ ID NO:11, 12, 14 or 16.

5. A multimeric protein as claimed in claim 4, wherein the multimer is cross-linked.

6. A composition comprising:
   a human hemoglobin protein as claimed in claim 1; and a pharmaceutically acceptable carrier or diluent.

7. The composition as claimed in claim 6, further comprising at least one reductant, optionally wherein the at least one reductant is ascorbate.

8. The composition as claimed in claim 6, wherein the composition is a blood substitute composition.

* * * * *

SEQUENCE LISTING

<160> NUMBER OF SEQ ID NOS: 18

<210> SEQ ID NO 1
<211> LENGTH: 146
<212> TYPE: PRT
<213> ORGANISM: Homo sapiens

<400> SEQUENCE: 1

-continued

```
Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145
```

<210> SEQ ID NO 2
<211> LENGTH: 141
<212> TYPE: PRT
<213> ORGANISM: Homo sapiens

<400> SEQUENCE: 2

```
Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140
```

<210> SEQ ID NO 3
<211> LENGTH: 146
<212> TYPE: PRT
<213> ORGANISM: Homo sapiens

<400> SEQUENCE: 3

```
Gly His Phe Thr Glu Glu Asp Lys Ala Thr Ile Thr Ser Leu Trp Gly
1               5                   10                  15

Lys Val Asn Val Glu Asp Ala Gly Gly Glu Thr Leu Gly Arg Leu Leu
            20                  25                  30
```

Val Val Tyr Pro Trp Thr Gln Arg Phe Phe Asp Ser Phe Gly Asn Leu
            35                  40                  45

Ser Ser Ala Ser Ala Ile Met Gly Asn Pro Lys Val Lys Ala His Gly
    50                  55                  60

Lys Lys Val Leu Thr Ser Leu Gly Asp Ala Ile Lys His Leu Asp Asp
65                  70                  75                  80

Leu Lys Gly Thr Phe Ala Gln Leu Ser Glu Leu His Cys Asp Lys Leu
                85                  90                  95

His Val Asp Pro Glu Asn Phe Lys Leu Leu Gly Asn Val Leu Val Thr
            100                 105                 110

Val Leu Ala Ile His Phe Gly Lys Glu Phe Thr Pro Glu Val Gln Ala
            115                 120                 125

Ser Trp Gln Lys Met Val Thr Ala Val Ala Ser Ala Leu Ser Ser Arg
    130                 135                 140

Tyr His
145

<210> SEQ ID NO 4
<211> LENGTH: 146
<212> TYPE: PRT
<213> ORGANISM: Homo sapiens

<400> SEQUENCE: 4

Gly His Phe Thr Glu Glu Asp Lys Ala Thr Ile Thr Ser Leu Trp Gly
1               5                   10                  15

Lys Val Asn Val Glu Asp Ala Gly Gly Glu Thr Leu Gly Arg Leu Leu
            20                  25                  30

Val Val Tyr Pro Trp Thr Gln Arg Phe Phe Asp Ser Phe Gly Asn Leu
            35                  40                  45

Ser Ser Ala Ser Ala Ile Met Gly Asn Pro Lys Val Lys Ala His Gly
    50                  55                  60

Lys Lys Val Leu Thr Ser Leu Gly Asp Ala Ile Lys His Leu Asp Asp
65                  70                  75                  80

Leu Lys Gly Thr Phe Ala Gln Leu Ser Glu Leu His Cys Asp Lys Leu
                85                  90                  95

His Val Asp Pro Glu Asn Phe Lys Leu Leu Gly Asn Val Leu Val Thr
            100                 105                 110

Val Leu Ala Ile His Phe Gly Lys Glu Phe Thr Pro Glu Val Gln Ala
            115                 120                 125

Ser Trp Gln Lys Met Val Thr Gly Val Ala Ser Ala Leu Ser Ser Arg
    130                 135                 140

Tyr His
145

<210> SEQ ID NO 5
<211> LENGTH: 146
<212> TYPE: PRT
<213> ORGANISM: Artificial Sequence
<220> FEATURE:
<223> OTHER INFORMATION: βV1M (reference protein)

<400> SEQUENCE: 5

Met His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

```
Val Val Tyr Pro Trp Thr Gln Arg Phe Phe Glu Ser Phe Gly Asp Leu
             35                  40                  45

Ser Thr Pro Asp Ala Val Met Gly Asn Pro Lys Val Lys Ala His Gly
 50                  55                  60

Lys Lys Val Leu Gly Ala Phe Ser Asp Gly Leu Ala His Leu Asp Asn
 65                  70                  75                  80

Leu Lys Gly Thr Phe Ala Thr Leu Ser Glu Leu His Cys Asp Lys Leu
                 85                  90                  95

His Val Asp Pro Glu Asn Phe Arg Leu Leu Gly Asn Val Leu Val Cys
                100                 105                 110

Val Leu Ala His His Phe Gly Lys Glu Phe Thr Pro Pro Val Gln Ala
                115                 120                 125

Ala Tyr Gln Lys Val Val Ala Gly Val Ala Asn Ala Leu Ala His Lys
            130                 135                 140

Tyr His
145
```

```
<210> SEQ ID NO 6
<211> LENGTH: 141
<212> TYPE: PRT
<213> ORGANISM: Artificial Sequence
<220> FEATURE:
<223> OTHER INFORMATION: αV1M mutant (reference protein)

<400> SEQUENCE: 6

Met Leu Ser Pro Ala Asp Lys Thr Asn Val Lys Ala Ala Trp Gly Lys
 1                   5                  10                  15

Val Gly Ala His Ala Gly Glu Tyr Gly Ala Glu Ala Leu Glu Arg Met
                 20                  25                  30

Phe Leu Ser Phe Pro Thr Thr Lys Thr Tyr Phe Pro His Phe Asp Leu
                 35                  40                  45

Ser His Gly Ser Ala Gln Val Lys Gly His Gly Lys Lys Val Ala Asp
 50                  55                  60

Ala Leu Thr Asn Ala Val Ala His Val Asp Asp Met Pro Asn Ala Leu
 65                  70                  75                  80

Ser Ala Leu Ser Asp Leu His Ala His Lys Leu Arg Val Asp Pro Val
                 85                  90                  95

Asn Phe Lys Leu Leu Ser His Cys Leu Leu Val Thr Leu Ala Ala His
                100                 105                 110

Leu Pro Ala Glu Phe Thr Pro Ala Val His Ala Ser Leu Asp Lys Phe
                115                 120                 125

Leu Ala Ser Val Ser Thr Val Leu Thr Ser Lys Tyr Arg
            130                 135                 140
```

```
<210> SEQ ID NO 7
<211> LENGTH: 146
<212> TYPE: PRT
<213> ORGANISM: Artificial Sequence
<220> FEATURE:
<223> OTHER INFORMATION: γ1G1M (reference protein)

<400> SEQUENCE: 7

Met His Phe Thr Glu Glu Asp Lys Ala Thr Ile Thr Ser Leu Trp Gly
 1                   5                  10                  15

Lys Val Asn Val Glu Asp Ala Gly Gly Glu Thr Leu Gly Arg Leu Leu
                 20                  25                  30

Val Val Tyr Pro Trp Thr Gln Arg Phe Phe Asp Ser Phe Gly Asn Leu
                 35                  40                  45
```

```
Ser Ser Ala Ser Ala Ile Met Gly Asn Pro Lys Val Lys Ala His Gly
        50                  55                  60

Lys Lys Val Leu Thr Ser Leu Gly Asp Ala Ile Lys His Leu Asp Asp
 65                  70                  75                  80

Leu Lys Gly Thr Phe Ala Gln Leu Ser Glu Leu His Cys Asp Lys Leu
                 85                  90                  95

His Val Asp Pro Glu Asn Phe Lys Leu Leu Gly Asn Val Leu Val Thr
                100                 105                 110

Val Leu Ala Ile His Phe Gly Lys Glu Phe Thr Pro Glu Val Gln Ala
            115                 120                 125

Ser Trp Gln Lys Met Val Thr Ala Val Ala Ser Ala Leu Ser Ser Arg
130                 135                 140

Tyr His
145

<210> SEQ ID NO 8
<211> LENGTH: 146
<212> TYPE: PRT
<213> ORGANISM: Artificial Sequence
<220> FEATURE:
<223> OTHER INFORMATION: γ2G1M (reference protein)

<400> SEQUENCE: 8

Met His Phe Thr Glu Glu Asp Lys Ala Thr Ile Thr Ser Leu Trp Gly
  1               5                  10                  15

Lys Val Asn Val Glu Asp Ala Gly Gly Glu Thr Leu Gly Arg Leu Leu
                20                  25                  30

Val Val Tyr Pro Trp Thr Gln Arg Phe Phe Asp Ser Phe Gly Asn Leu
            35                  40                  45

Ser Ser Ala Ser Ala Ile Met Gly Asn Pro Lys Val Lys Ala His Gly
        50                  55                  60

Lys Lys Val Leu Thr Ser Leu Gly Asp Ala Ile Lys His Leu Asp Asp
 65                  70                  75                  80

Leu Lys Gly Thr Phe Ala Gln Leu Ser Glu Leu His Cys Asp Lys Leu
                 85                  90                  95

His Val Asp Pro Glu Asn Phe Lys Leu Leu Gly Asn Val Leu Val Thr
                100                 105                 110

Val Leu Ala Ile His Phe Gly Lys Glu Phe Thr Pro Glu Val Gln Ala
            115                 120                 125

Ser Trp Gln Lys Met Val Thr Gly Val Ala Ser Ala Leu Ser Ser Arg
130                 135                 140

Tyr His
145

<210> SEQ ID NO 9
<211> LENGTH: 146
<212> TYPE: PRT
<213> ORGANISM: Artificial Sequence
<220> FEATURE:
<223> OTHER INFORMATION: βT84Y modified haemoglobin subunit

<400> SEQUENCE: 9

Val His Leu Thr Pro Glu Glu Lys Ser Ala Val Thr Ala Leu Trp Gly
  1               5                  10                  15

Lys Val Asn Val Asp Glu Val Gly Gly Glu Ala Leu Gly Arg Leu Leu
                20                  25                  30

Val Val Tyr Pro Trp Thr Gln Arg Phe Phe Glu Ser Phe Gly Asp Leu
```

```
                    35                  40                  45

Ser Thr Pro Asp Ala Val Met Gly Asn Pro Lys Val Lys Ala His Gly
         50                  55                  60

Lys Lys Val Leu Gly Ala Phe Ser Asp Gly Leu Ala His Leu Asp Asn
 65                  70                  75                  80

Leu Lys Gly Tyr Phe Ala Thr Leu Ser Glu Leu His Cys Asp Lys Leu
                 85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 10
<211> LENGTH: 146
<212> TYPE: PRT
<213> ORGANISM: Artificial Sequence
<220> FEATURE:
<223> OTHER INFORMATION: βT84Y modified haemoglobin subunit (V1M mutant)

<400> SEQUENCE: 10

Met His Leu Thr Pro Glu Glu Lys Ser Ala Val Thr Ala Leu Trp Gly
 1               5                  10                  15

Lys Val Asn Val Asp Glu Val Gly Gly Glu Ala Leu Gly Arg Leu Leu
             20                  25                  30

Val Val Tyr Pro Trp Thr Gln Arg Phe Phe Glu Ser Phe Gly Asp Leu
         35                  40                  45

Ser Thr Pro Asp Ala Val Met Gly Asn Pro Lys Val Lys Ala His Gly
     50                  55                  60

Lys Lys Val Leu Gly Ala Phe Ser Asp Gly Leu Ala His Leu Asp Asn
 65                  70                  75                  80

Leu Lys Gly Tyr Phe Ala Thr Leu Ser Glu Leu His Cys Asp Lys Leu
                 85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 11
<211> LENGTH: 141
<212> TYPE: PRT
<213> ORGANISM: Artificial Sequence
<220> FEATURE:
<223> OTHER INFORMATION: αL91Y modified haemoglobin subunit (V1M mutant)

<400> SEQUENCE: 11

Met Leu Ser Pro Ala Asp Lys Thr Asn Val Lys Ala Ala Trp Gly Lys
 1               5                  10                  15

Val Gly Ala His Ala Gly Glu Tyr Gly Ala Glu Ala Leu Glu Arg Met
             20                  25                  30
```

```
Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
 65                  70                  75                  80

Ser Ala Leu Ser Asp Leu His Ala His Lys Tyr Arg Val Asp Pro Val
                85                  90                  95

Asn Phe Lys Leu Leu Ser His Cys Leu Leu Val Thr Leu Ala Ala His
                100                 105                 110

Leu Pro Ala Glu Phe Thr Pro Ala Val His Ala Ser Leu Asp Lys Phe
            115                 120                 125

Leu Ala Ser Val Ser Thr Val Leu Thr Ser Lys Tyr Arg
        130                 135                 140

<210> SEQ ID NO 12
<211> LENGTH: 141
<212> TYPE: PRT
<213> ORGANISM: Artificial Sequence
<220> FEATURE:
<223> OTHER INFORMATION: αL91Y modified haemoglobin subunit

<400> SEQUENCE: 12

Val Leu Ser Pro Ala Asp Lys Thr Asn Val Lys Ala Ala Trp Gly Lys
  1               5                  10                  15

Val Gly Ala His Ala Gly Glu Tyr Gly Ala Glu Ala Leu Glu Arg Met
                 20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
 65                  70                  75                  80

Ser Ala Leu Ser Asp Leu His Ala His Lys Tyr Arg Val Asp Pro Val
                85                  90                  95

Asn Phe Lys Leu Leu Ser His Cys Leu Leu Val Thr Leu Ala Ala His
                100                 105                 110

Leu Pro Ala Glu Phe Thr Pro Ala Val His Ala Ser Leu Asp Lys Phe
            115                 120                 125

Leu Ala Ser Val Ser Thr Val Leu Thr Ser Lys Tyr Arg
        130                 135                 140

<210> SEQ ID NO 13
<211> LENGTH: 146
<212> TYPE: PRT
<213> ORGANISM: Artificial Sequence
<220> FEATURE:
<223> OTHER INFORMATION: γ2L96Y modified haemoglobin subunit (G1M
      Mutant)

<400> SEQUENCE: 13

Met His Phe Thr Glu Glu Asp Lys Ala Thr Ile Thr Ser Leu Trp Gly
  1               5                  10                  15

Lys Val Asn Val Glu Asp Ala Gly Gly Glu Thr Leu Gly Arg Leu Leu
                 20                  25                  30

Val Val Tyr Pro Trp Thr Gln Arg Phe Phe Asp Ser Phe Gly Asn Leu
        35                  40                  45

Ser Ser Ala Ser Ala Ile Met Gly Asn Pro Lys Val Lys Ala His Gly
```

```
                    50                  55                  60
Lys Lys Val Leu Thr Ser Leu Gly Asp Ala Ile Lys His Leu Asp Asp
 65                  70                  75                  80

Leu Lys Gly Thr Phe Ala Gln Leu Ser Glu Leu His Cys Asp Lys Tyr
                 85                  90                  95

His Val Asp Pro Glu Asn Phe Lys Leu Leu Gly Asn Val Leu Val Thr
            100                 105                 110

Val Leu Ala Ile His Phe Gly Lys Glu Phe Thr Pro Glu Val Gln Ala
        115                 120                 125

Ser Trp Gln Lys Met Val Thr Gly Val Ala Ser Ala Leu Ser Ser Arg
    130                 135                 140

Tyr His
145

<210> SEQ ID NO 14
<211> LENGTH: 141
<212> TYPE: PRT
<213> ORGANISM: Artificial Sequence
<220> FEATURE:
<223> OTHER INFORMATION: αL29F modified haemoglobin subunit (V1M mutant)

<400> SEQUENCE: 14

Met Leu Ser Pro Ala Asp Lys Thr Asn Val Lys Ala Ala Trp Gly Lys
  1               5                  10                  15

Val Gly Ala His Ala Gly Glu Tyr Gly Ala Glu Ala Phe Glu Arg Met
                 20                  25                  30

Phe Leu Ser Phe Pro Thr Thr Lys Thr Tyr Phe Pro His Phe Asp Leu
             35                  40                  45

Ser His Gly Ser Ala Gln Val Lys Gly His Gly Lys Lys Val Ala Asp
         50                  55                  60

Ala Leu Thr Asn Ala Val Ala His Val Asp Asp Met Pro Asn Ala Leu
 65                  70                  75                  80

Ser Ala Leu Ser Asp Leu His Ala His Lys Leu Arg Val Asp Pro Val
                 85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 15
<211> LENGTH: 146
<212> TYPE: PRT
<213> ORGANISM: Artificial Sequence
<220> FEATURE:
<223> OTHER INFORMATION: γ2V67F modified haemoglobin subunit (G1M
      Mutant)

<400> SEQUENCE: 15

Met His Phe Thr Glu Glu Asp Lys Ala Thr Ile Thr Ser Leu Trp Gly
  1               5                  10                  15

Lys Val Asn Val Glu Asp Ala Gly Gly Glu Thr Leu Gly Arg Leu Leu
                 20                  25                  30

Val Val Tyr Pro Trp Thr Gln Arg Phe Phe Asp Ser Phe Gly Asn Leu
             35                  40                  45

Ser Ser Ala Ser Ala Ile Met Gly Asn Pro Lys Val Lys Ala His Gly
         50                  55                  60
```

```
Lys Lys Phe Leu Thr Ser Leu Gly Asp Ala Ile Lys His Leu Asp Asp
 65                  70                  75                  80

Leu Lys Gly Thr Phe Ala Gln Leu Ser Glu Leu His Cys Asp Lys Leu
                 85                  90                  95

His Val Asp Pro Glu Asn Phe Lys Leu Leu Gly Asn Val Leu Val Thr
            100                 105                 110

Val Leu Ala Ile His Phe Gly Lys Glu Phe Thr Pro Glu Val Gln Ala
        115                 120                 125

Ser Trp Gln Lys Met Val Thr Gly Val Ala Ser Ala Leu Ser Ser Arg
    130                 135                 140

Tyr His
145

<210> SEQ ID NO 16
<211> LENGTH: 141
<212> TYPE: PRT
<213> ORGANISM: Artificial Sequence
<220> FEATURE:
<223> OTHER INFORMATION: αL29F and αL91Y modified haemoglobin subunit
      (V1M mutant)

<400> SEQUENCE: 16

Met Leu Ser Pro Ala Asp Lys Thr Asn Val Lys Ala Ala Trp Gly Lys
  1               5                  10                  15

Val Gly Ala His Ala Gly Glu Tyr Gly Ala Glu Ala Phe Glu Arg Met
                 20                  25                  30

Phe Leu Ser Phe Pro Thr Thr Lys Thr Tyr Phe Pro His Phe Asp Leu
             35                  40                  45

Ser His Gly Ser Ala Gln Val Lys Gly His Gly Lys Lys Val Ala Asp
         50                  55                  60

Ala Leu Thr Asn Ala Val Ala His Val Asp Asp Met Pro Asn Ala Leu
 65                  70                  75                  80

Ser Ala Leu Ser Asp Leu His Ala His Lys Tyr Arg Val Asp Pro Val
                 85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 17
<211> LENGTH: 146
<212> TYPE: PRT
<213> ORGANISM: Artificial Sequence
<220> FEATURE:
<223> OTHER INFORMATION: γ2V67F and γ2L96Y modified haemoglobin subunit
      (G1M Mutant)

<400> SEQUENCE: 17

Met His Phe Thr Glu Glu Asp Lys Ala Thr Ile Thr Ser Leu Trp Gly
  1               5                  10                  15

Lys Val Asn Val Glu Asp Ala Gly Gly Glu Thr Leu Gly Arg Leu Leu
                 20                  25                  30

Val Val Tyr Pro Trp Thr Gln Arg Phe Phe Asp Ser Phe Gly Asn Leu
             35                  40                  45

Ser Ser Ala Ser Ala Ile Met Gly Asn Pro Lys Val Lys Ala His Gly
         50                  55                  60
```

```
Lys Lys Phe Leu Thr Ser Leu Gly Asp Ala Ile Lys His Leu Asp Asp
 65                  70                  75                  80

Leu Lys Gly Thr Phe Ala Gln Leu Ser Glu Leu His Cys Asp Lys Tyr
                 85                  90                  95

His Val Asp Pro Glu Asn Phe Lys Leu Leu Gly Asn Val Leu Val Thr
            100                 105                 110

Val Leu Ala Ile His Phe Gly Lys Glu Phe Thr Pro Glu Val Gln Ala
        115                 120                 125

Ser Trp Gln Lys Met Val Thr Gly Val Ala Ser Ala Leu Ser Ser Arg
    130                 135                 140

Tyr His
145

<210> SEQ ID NO 18
<211> LENGTH: 153
<212> TYPE: PRT
<213> ORGANISM: Artificial Sequence
<220> FEATURE:
<223> OTHER INFORMATION: Human myoglobin

<400> SEQUENCE: 18

Gly Leu Ser Asp Gly Glu Trp Gln Leu Val Leu Asn Val Trp Gly Lys
  1               5                  10                  15

Val Glu Ala Asp Ile Pro Gly His Gly Gln Glu Val Leu Ile Arg Leu
             20                  25                  30

Phe Lys Gly His Pro Glu Thr Leu Glu Lys Phe Asp Lys Phe Lys His
         35                  40                  45

Leu Lys Ser Glu Asp Glu Met Lys Ala Ser Glu Asp Leu Lys Lys His
 50                  55                  60

Gly Ala Thr Val Leu Thr Ala Leu Gly Gly Ile Leu Lys Lys Lys Gly
 65                  70                  75                  80

His His Glu Ala Glu Ile Lys Pro Leu Ala Gln Ser His Ala Thr Lys
             85                  90                  95

His Lys Ile Pro Val Lys Tyr Leu Glu Phe Ile Ser Glu Cys Ile Ile
            100                 105                 110

Gln Val Leu Gln Ser Lys His Pro Gly Asp Phe Gly Ala Asp Ala Gln
        115                 120                 125

Gly Ala Met Asn Lys Ala Leu Glu Leu Phe Arg Lys Asp Met Ala Ser
    130                 135                 140

Asn Tyr Lys Glu Leu Gly Phe Gln Gly
145                 150
```